(12) United States Patent
Yuds et al.

(10) Patent No.: US 11,577,012 B2
(45) Date of Patent: Feb. 14, 2023

(54) AUTO ADJUSTMENT OF BLOOD TREATMENT PARAMETERS BASED ON PATIENT COMFORT

(71) Applicant: Fresenius Medical Care Holdings, Inc., Waltham, MA (US)

(72) Inventors: David Yuds, Hudson, NH (US); Eric Bergman, Newton, MA (US); Ken Chhi, Fremont, CA (US); Stephen Merchant, Oklahoma City, OK (US); Christopher Yim Chau, Mission, TX (US); Roland Levin, San Ramon, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 371 days.

(21) Appl. No.: 16/417,837

(22) Filed: May 21, 2019

(65) Prior Publication Data

US 2020/0368418 A1 Nov. 26, 2020

(51) Int. Cl.
| | |
|---|---|
| *A61M 1/16* | (2006.01) |
| *A61M 1/36* | (2006.01) |
| *A61B 5/00* | (2006.01) |
| *G16H 20/17* | (2018.01) |

(52) U.S. Cl.
CPC ......... *A61M 1/1603* (2014.02); *A61B 5/4836* (2013.01); *A61M 1/3607* (2014.02); *A61M 2205/502* (2013.01); *A61M 2230/005* (2013.01); *G16H 20/17* (2018.01)

(58) Field of Classification Search
CPC ..... A61B 5/4836; A61M 1/16; A61M 1/1603; A61M 1/28; A61M 1/3403; A61M 1/3607; A61M 2205/502; A61M 2205/505; A61M 2230/005; G16H 20/17; G16H 20/40; G16H 40/63
See application file for complete search history.

(56) References Cited

U.S. PATENT DOCUMENTS

| | | | |
|---|---|---|---|
| 9,526,820 B2 | 12/2016 | Beiriger et al. | |
| 2013/0211206 A1 | 8/2013 | Sands et al. | |
| 2015/0148697 A1* | 5/2015 | Burnes | A61B 5/145 600/513 |
| 2016/0199562 A1 | 7/2016 | Parisotto et al. | |
| 2017/0326284 A1* | 11/2017 | Dulsner | G16H 40/63 |
| 2018/0185566 A1* | 7/2018 | Hakansson | A61B 5/6866 |
| 2018/0193548 A1* | 7/2018 | Hakansson | G16H 40/63 |

OTHER PUBLICATIONS

Blake, "Drain pain, overfill, and how they are connected", Peritoneal Dialysis International 34(4):342-344, Jun. 2014.
Nuvvula, "Learned helplessness", Contemporary clinical dentistry 7(4):426, Oct. 2016.
(Continued)

*Primary Examiner* — Dirk R Bass
(74) *Attorney, Agent, or Firm* — Fish & Richardson P.C.

(57) ABSTRACT

A blood treatment machine includes a patient comfort feedback mechanism configured to be adjusted by a patient to indicate comfort levels of the patient. The machine is configured to adjust one or more treatment parameters based on the patient feedback.

29 Claims, 13 Drawing Sheets

(56) References Cited

OTHER PUBLICATIONS health.harvard.edu [online] "How your attitudes affect your health", Harvard Health Publications, Harvard Women's Health Watch, Retrieved from the Internet <https://www.health.harvard.edu/mind-and-mood/how-your-attitudes-affect-your-health>, May 2016, 2 pages.

PCT International Search Report and Written Opinion in Application No. PCT/US2020/029136, dated Jul. 9, 2020, 12 pages.

Chu et al., "Physiological Signal-Based Method for Measurement of Pain Intensity," Front Neurosci., May 2017, 11(279):1-13.

* cited by examiner

AUTO ADJUSTMENT OF BLOOD TREATMENT PARAMETERS BASED ON PATIENT COMFORT

TECHNICAL FIELD

This disclosure relates to auto adjustment of blood treatment parameters based on patient comfort.

BACKGROUND

Dialysis is a treatment used to support a patient with insufficient renal function. The two principal dialysis methods include hemodialysis (HD) and peritoneal dialysis (PD). During HD, the patient's blood is passed through a dialyzer of a dialysis machine, while a dialysis solution (or, dialysate) is also passed through the dialyzer. A semi-permeable membrane in the dialyzer separates the blood from the dialysate and allows fluid exchanges to take place between the dialysate and the blood stream via diffusion, osmosis, and convective flow. These exchanges across the membrane result in the removal of waste products (e.g., such as solutes, like urea and creatinine) from the blood. These exchanges also regulate the levels of other substances (e.g., sodium and water) in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products (e.g., such as solutes, like urea and creatinine) from the blood and regulate the levels of other substances (e.g., sodium and water) in the blood.

SUMMARY

In some aspects, a blood treatment machine includes a patient comfort feedback mechanism configured to be adjusted by a patient to indicate comfort levels of the patient and to generate patient feedback data, and a signal transceiver configured to send the patient feedback data to a controller of the blood treatment machine. The controller is configured to receive patient feedback data from the signal transceiver and adjust a treatment parameter based on the patient feedback data.

In some embodiments, the treatment parameter is an ultrafiltration rate.

In some embodiments, the controller lowers the ultrafiltration rate in response to patient discomfort indicated by the patient comfort feedback mechanism.

In some embodiments, the blood treatment machine includes a user interface, controlled by the controller.

In some embodiments, the controller displays the patient feedback data on the user interface of the blood treatment machine.

In some embodiments, the patient comfort feedback mechanism is adjusted using a mechanical input on the blood treatment machine.

In some embodiments, the user interface is a touchscreen.

In some embodiments, the patient comfort feedback mechanism is adjusted using inputs on the touchscreen.

In some embodiments, the patient comfort feedback mechanism is adjusted using a mechanical input on the blood treatment machine.

In some embodiments, the mechanical input is at least two buttons, a slider, or a dial.

In some embodiments, the patient comfort feedback mechanism is a mechanical input mounted on a housing of the blood treatment machine.

In some embodiments, the patient comfort feedback mechanism includes icons that correspond to a discomfort level of the patient.

In some embodiments, the patient comfort feedback mechanism is mounted on a body connected to the blood treatment machine by a wire.

In some embodiments, the patient comfort feedback mechanism provides at least three patient comfort levels.

In some embodiments, the blood treatment machine is a hemodialysis machine.

In some embodiments, the blood treatment machine is a peritoneal dialysis machine.

In certain aspects, a system for blood treatment includes a blood treatment machine. The blood treatment machine includes a signal transceiver configured to send and receive signals, and a controller configured to control the blood treatment machine and adjust a treatment parameter based on patient feedback data. The system further includes a patient comfort feedback mechanism connected to the blood treatment machine. The patient comfort feedback mechanism includes a patient interface configured to be adjusted by a patient to indicate comfort levels of the patient and to generate the patient feedback data, and a signal transceiver configured to send the patient feedback data to the controller of the blood treatment machine.

In some embodiments, the patient comfort feedback mechanism is wirelessly connected to the blood treatment machine.

In some embodiments, the treatment parameter is an ultrafiltration rate.

In some embodiments, the controller reduces the ultrafiltration rate in response to patient discomfort indicated by the patient comfort feedback mechanism.

In some embodiments, the controller displays the patient feedback data on a user interface of the blood treatment machine.

In some embodiments, the patient comfort feedback mechanism provides at least three patient comfort levels.

In certain aspects, a method for blood treatment includes performing blood treatment, receiving patient input related to a discomfort level of a patient via a patient comfort feedback mechanism, and adjusting a parameter of the blood treatment based on the patient input.

In some embodiments, the adjusting the parameter of the blood treatment includes adjusting at least one of an ultrafiltration rate, a pump rate, a dialysate dwell time, a drain percentage, fluid temperatures, a treatment time, and patient pressures.

The blood treatment machine includes a patient comfort feedback mechanism that receives input from a patient that indicates the discomfort level of the patient. The blood treatment machine then adjusts a parameter that can reduce patient discomfort. The machine can increase patient comfort when performing blood treatment based on real time, subjective patient input. The patient comfort feedback mechanism can then reduce patient discomfort and may reduce psychological aversion to blood treatment in general by providing repeatedly comfortable treatments.

The details of one or more embodiments of the invention are set forth in the accompanying drawings and the description below. Other aspects, features, and advantages of the invention will be apparent from the description and drawings, and from the claims.

DESCRIPTION OF DRAWINGS

Like reference symbols in the various drawings indicate like elements.

DETAILED DESCRIPTION

Figure 1A:
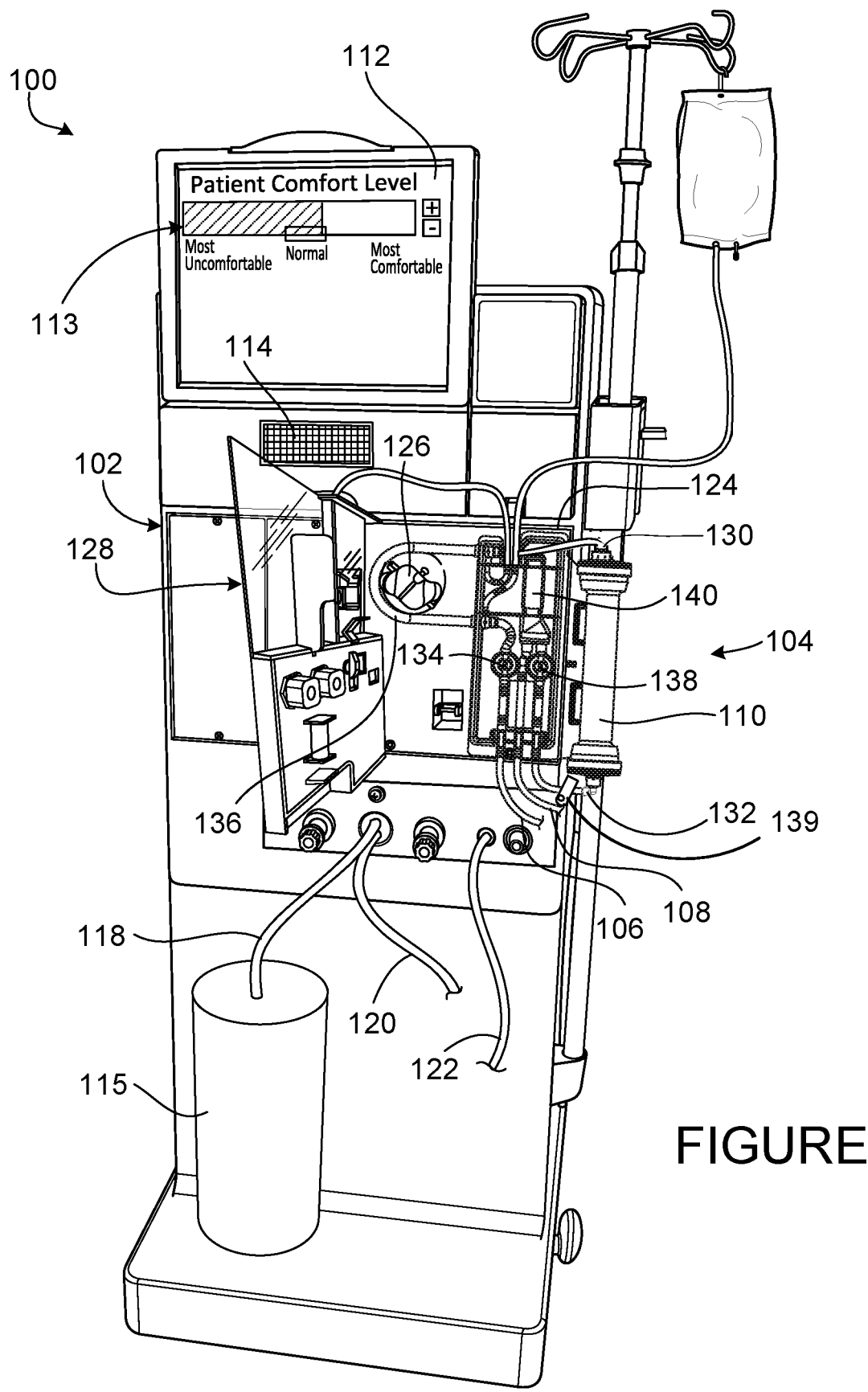
FIG. 1A is a perspective view of a blood treatment machine including a user interface with a patient comfort feedback mechanism.

Referring to FIG. 1A, a hemodialysis system 100 includes a blood treatment machine (hemodialysis machine 102) to which a disposable blood component set 104 that forms a blood circuit is releasably connected. During hemodialysis, arterial and venous patient lines 106, 108 of the blood component set 104 are connected to a patient and blood is circulated through various bloodlines and components, including a dialyzer 110, of the blood component set 104. At the same time, dialysate is circulated through a dialysate circuit formed by the dialyzer 110 and various other dialysate components and dialysate lines connected to the hemodialysis machine 102. Many of these dialysate components and dialysate lines are located inside the housing of the hemodialysis machine 102, and are thus not visible in FIG. 1A. The dialysate passes through the dialyzer 110 along with the blood. The blood and dialysate passing through the dialyzer 110 are separated from one another by a semipermeable structure (e.g., a semi-permeable membrane and/or semi-permeable microtubes) of the dialyzer 110. As a result of this arrangement, toxins are removed from the patient's blood and collected in the dialysate. The filtered blood exiting the dialyzer 110 is returned to the patient. The dialysate that exits the dialyzer 110 includes toxins removed from the blood and is commonly referred to as "spent dialysate." The spent dialysate is routed from the dialyzer 110 to a drain.

Still referring to FIG. 1A, the hemodialysis machine 102 includes a user interface 112 in the form of a touch screen. The user interface 112 allows the operator to input various different treatment parameters to the hemodialysis machine 102 and to otherwise control the hemodialysis machine 102. In addition, the user interface 112 serves as a display to convey information to the operator of the hemodialysis system 100. A patient comfort feedback mechanism 113 is displayed on the user interface 112. The patient comfort feedback mechanism 113 is used to adjust treatment parameters based on the subjective comfort level of the patient. Adjusting the parameters of the treatment also influences the total time of the treatment and the intensity of the treatment. Indicating discomfort can result in a longer, more gentle treatment, while indicating comfort can result in no change or a shorter, more intense treatment.

A speaker 114 is positioned below the user interface 112 and functions to provide audio signals to the operator of the system 100. Thus, the hemodialysis machine 102 is capable of providing both visual alerts via the user interface 112 and audio alerts via the speaker 114 to the operator of the system 100 during use. While the speaker 114 has been described as being positioned below the user interface 112, it should be appreciated that the speaker 114 could be positioned at any of various other locations on the hemodialysis machine 102.

As shown in FIG. 1A, a dialysate container 115 is connected to the hemodialysis machine 102 via a dialysate supply line 118. A drain line 120 and an ultrafiltration line 122 also extend from the hemodialysis machine 102. The dialysate supply line 118, the drain line 120, and the ultrafiltration line 122 are fluidly connected to the various dialysate components and dialysate lines inside the housing of the hemodialysis machine 102 that form part of the dialysate circuit. During hemodialysis, the dialysate supply line 118 carries fresh dialysate from the dialysate container 115 to the portion of the dialysate circuit located inside the hemodialysis machine 102. As noted above, the fresh dialysate is circulated through various dialysate lines and dialysate components, including the dialyzer 110, that form the dialysate circuit. As the dialysate passes through the dialyzer 110, it collects toxins from the patient's blood. The resulting spent dialysate is carried from the dialysate circuit to a drain via the drain line 120. When ultrafiltration is performed during treatment, a combination of the spent dialysate and excess fluid drawn from the patient is carried to the drain via the ultrafiltration line 122. In some embodiments, the ultrafiltration rate is adjustable using the patient comfort feedback mechanism 113 displayed on the user interface 112.

The blood component set 104 is secured to a module 124 attached to the front of the hemodialysis machine 102. The module 124 includes a blood pump 126 capable of driving blood through the blood circuit at a predetermined blood flow rate.

The module 124 also includes various other instruments capable of monitoring the blood flowing through the blood circuit. The module 124 includes a door 128 (shown in in the open state in FIG. 1A) that when closed cooperates with the front face of the module 124 to form a compartment sized and shaped to receive the blood component set 104. In the closed position, the door 128 presses certain blood components of the blood component set 104 against corresponding instruments exposed on the front face of the module 124.

Suitable blood component sets and their related components are described in greater detail in U.S. Pat. No. 9,526,820, entitled "Dialysis Systems, Components, and Methods," which is incorporated by reference herein.

Still referring to FIG. 1A, the dialysate circuit is formed by multiple dialysate components and dialysate lines positioned inside the housing of the hemodialysis machine 102 as well as the dialyzer 110, a dialyzer inlet line 130, and a dialyzer outlet line 132 that are positioned outside of the housing of the hemodialysis machine 102. The dialyzer inlet line 130 includes a connector adapted to connect to one end of the dialyzer 110, and the dialyzer outlet line 132 includes a connector adapted to connect to another end of the dialyzer 110.

Figure 1B:
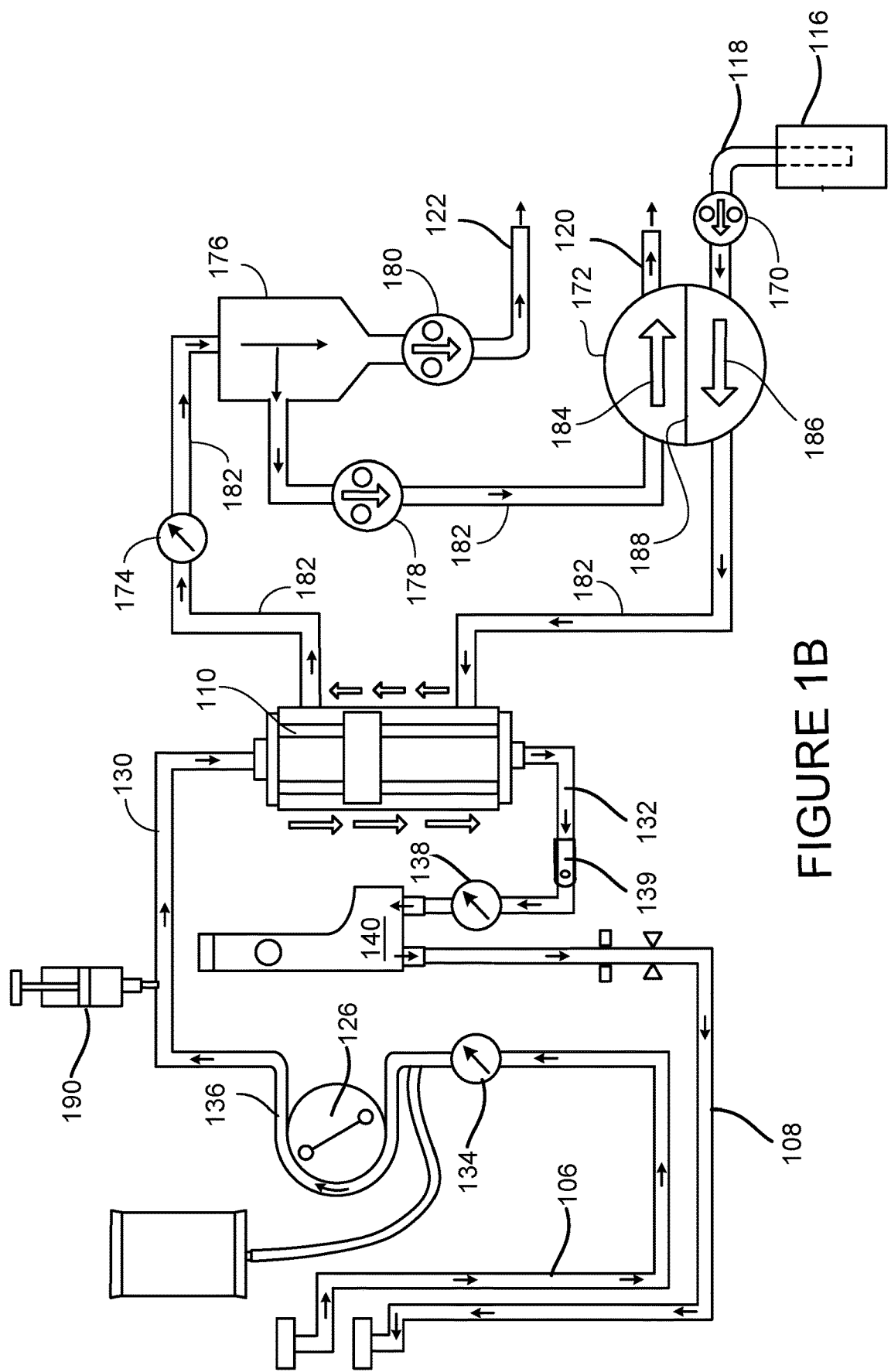
FIG. 1B is a schematic showing the flow paths of fluids into, through, and out of a blood circuit and a dialysate circuit of the blood treatment machine of FIG. 1A.

FIG. 1B is a schematic showing the flow paths of fluids into, through, and out of the blood circuit and the dialysate circuit of the hemodialysis system 100. Referring to the right side of FIG. 1B, dialysate components of the dialysate circuit that are located inside the housing of the hemodialysis machine 102 include a first dialysate pump 170, a balancing device 172, a pressure sensor 174, an equalizing chamber 176, a second dialysate pump 178, and an ultrafiltration pump 180. These dialysate components are fluidly connected to one another via a series of dialysate lines 182.

The dialysate pump 170 is capable of pumping dialysate to the balancing chamber via the dialysate supply line 118. In some implementations, the dialysate pump 170 is a peristaltic pump. However, any various other types of pumps can alternatively or additionally be used. Examples of other suitable types of pumps include diaphragm pumps and gear pumps. In some embodiments, the dialysate pump rate is adjustable using the patient comfort feedback mechanism 113 displayed on the user interface 112.

The balancing device 172 includes a spherical chamber that is divided into a first chamber half 184 and a second chamber half 186 by a flexible membrane 188. As fluid flows into the first chamber half 184, fluid is forced out of the second chamber half 186, and vice versa. This balancing device 172 construction helps to ensure that the volume of fluid entering the balancing device 172 is equal to the volume of fluid exiting the balancing device 172. This helps to ensure that the volume of fresh dialysate entering the dialysate circuit is equal to the volume of spent dialysate exiting the dialysate circuit when desired during treatment, as described in greater detail below.

During hemodialysis, the dialysate exiting the second chamber half 186 is directed through the dialyzer 110 toward the equalizing chamber 176. The pressure sensor located along the dialysate line connecting the dialyzer 110 to the equalizing chamber 176 is adapted to measure the pressure of the spent dialysate exiting the dialyzer 110. Any of various different types of pressure sensors capable of measuring the pressure of the spent dialysate passing from the dialyzer 110 to the equalizing chamber 176 can be used.

The spent dialysate collects in the equalizing chamber 176. The dialysate pump 178 is configured to pump the spent dialysate from the equalizing chamber 176 to the first chamber half 184 of the balancing device 172. In some implementations, the dialysate pump 178 is a peristaltic pump. However, any various other types of pumps can alternatively or additionally be used. Examples of other suitable types of pumps include diaphragm pumps and gear pumps. As the first chamber half 184 of the balancing device 172 fills with the spent dialysate, fresh dialysate within the second chamber half 186 is expelled toward dialyzer 110. Subsequently, as the second chamber half 186 is refilled with fresh dialysate, the spent dialysate within the first chamber half 184 is forced through the drain line 120 to the drain.

The ultrafiltration line 122 is connected to an outlet of the equalizing chamber 176. The ultrafiltration pump 180 is operatively connected to the ultrafiltration line 122 such that when the ultrafiltration pump 180 is operated, spent dialysate can be pulled from the equalizing chamber 176 and directed to the drain via the ultrafiltration line 122. Operation of the ultrafiltration pump 180 while simultaneously operating the dialysate pump 178 causes increased vacuum pressure within the portion of the dialysate line 182 connecting the equalizing chamber 176 to the dialyzer 110, and thus creates increased vacuum pressure within the dialyzer 110. As a result of this increased vacuum pressure, additional fluid is pulled from the blood circuit into the dialysate circuit across the semi-permeable structure (e.g., semi-permeable membrane or semi-permeable microtubes) of the dialyzer 110. The ultrafiltration pump 180 can therefore control the volume of fluid being pulled from the patient via the blood circuit. The ultrafiltration rate of FIG. 1A can be adjusted during treatment using the patient comfort feedback mechanism 113 on the user interface 112.

In certain implementations, the ultrafiltration pump 180 is a peristaltic pump. However, any various other types of pumps can alternatively or additionally be used. Examples of other suitable types of pumps include diaphragm pumps and gear pumps. However, any various other types of pumps can alternatively or additionally be used. Examples of other suitable types of pumps include diaphragm pumps and gear pumps. The rate at which the ultrafiltration pump moves fluid is called the ultrafiltration (UF) rate.

During hemodialysis, the blood pump 126 is activated causing blood to circulate through the blood circuit. The blood is drawn from the patient via an arterial patient line 106 and flows to the arterial pressure sensor capsule 134. An arterial pressure sensor (not shown) on the front face of the module 124 aligns with the arterial pressure sensor capsule 134 and measures the pressure of the blood flowing through the blood circuit on the arterial side. The blood then flows through the U-shaped pump line 136, which is operatively engaged with the blood pump 126. From the pump line 136, the blood flows to the dialyzer 110. In certain implementations, a drug, such as heparin, is injected into the blood via a syringe pump. Injecting heparin into the blood can help to prevent blood clots from forming within the blood circuit. Other types of drugs can alternatively or additionally be injected into the blood circuit using the syringe pump. Examples of such drugs include vitamin D and iron supplements, such as Venofer® and Epogen®. In some embodiments, the drug flow rate and/or drug concertation is adjustable using the patient comfort feedback mechanism 113 displayed on the user interface 112.

A crit line sensor 139 is disposed at the outlet of the dialyzer 110 and measures the level of hematocrit in the blood exiting the dialyzer 110 and returning to the patient. Hematocrit is the ratio of the volume of red blood cells to the total volume of blood, usually provided as a percentage. A higher hematocrit measurement means that the volume of blood is decreasing because fluid is being removed during dialysis. Thus, with red blood cells remaining at the same level, the total volume of blood decreases. The crit line sensor 139 on the dialyzer outlet line 132, uses an optical sensor to measure the hematocrit in a small sample of blood flowing through the extracorporeal blood circuit, specifically the blood exiting the dialyzer 110 via the venous bloodline.

After exiting the dialyzer 110, the blood flows through a venous pressure sensor capsule 138 where the pressure of the blood on the venous side is measured by an associated pressure sensor on the front face of the module 124. Next, the blood flows through the entry port of an air release device 140 in which any gas, such as air, in the blood can escape and can be vented to atmosphere via a vent at the top of the air release device 140.

After exiting the air release device 140, the blood travels through the venous patient line 108 and back to the patient.

Turning now to the dialysate circuit shown in FIG. 1B, during hemodialysis, fresh dialysate is pumped into the dialysate circuit from the dialysate container 115 via the dialysate supply line 118 by running the dialysate pump. The fresh dialysate enters the second chamber half 186 of the balancing device 172. As spent dialysate enters the first chamber half 186 of the balancing device 172, the fresh dialysate is forced out of the second chamber half 186 and toward the dialyzer 110 via the dialysate line. The dialysate passes through the dialyzer 110 at the same time that the patient's blood is passed through the dialyzer 110 on an opposite side of the semi-permeable structure of the dialyzer 110. As a result, toxins, such as urea, are transferred across a permeable structure (e.g., permeable membrane and/or permeable microtubes) of the dialyzer 110 from the patient's blood to the dialysate, and those toxins collect in the dialysate forming spent dialysate. The spent dialysate exiting the dialyzer 110 is circulated through the dialysate circuit to the equalizing chamber 176. The dialysate pump 178 draws spent dialysate from the equalizing chamber 176 and delivers it to the first chamber half 184 of the balancing device 172. As the spent dialysate fills the first chamber half 184, fresh dialysate within the second chamber have is delivered to the dialyzer 110. As the second chamber half 186 is subsequently refilled with fresh dialysate, the spent dialysate within the first chamber half 184 is forced out of the balancing device 172 and into a drain via the drain line 120. The balancing device 172 balances the dialysate entering the dialysate circuit with the dialysate exiting the dialysate circuit to ensure that a substantially constant volume of dialysate remains within the dialysate circuit when ultrafiltration is not being performed.

In certain treatments, an ultrafiltration process is performed to remove excess fluid from the patient's blood. During ultrafiltration, a pressure gradient is created across the permeable structure between the dialysate side and the blood side of the dialyzer 110 by running the ultrafiltration pump 180. As a result, fluid is drawn across the semi-permeable structure of the dialyzer 110 from the blood circuit to the dialysate circuit. Spent dialysate, including the toxins and excess fluid drawn from the patient, is drawn from the equalizing chamber by the ultrafiltration pump 180 and is delivered to the drain via the ultrafiltration line 122.

Conducting a treatment with a UF rate that is too high can lead to patient discomfort. Referring again to FIG. 1A, when the patient experiences discomfort, he/she or the patient's clinician can indicate this discomfort by adjusting the patient comfort feedback mechanism. The UF rate can be adjusted accordingly.

In use, the hemodialysis machine 102 is prepped and primed by installing the U shaped bloodline 136 around the blood pump 126 and installing the patient onto the extracorporeal blood circuit as described above. The hemodialysis machine 102 prep also requires an operator to input a prescription that includes various parameters, including ultrafiltration rate, dosage of heparin, blood pump rate, dialysate flow rate, drug flow rate, and other information relating to the prescription. Some information, like dialysate temperature and concentration of salts within the dialysate are predetermined by the hemodialysis machine 102. The operator also selects ranges of patient and treatment parameters that, if the parameter is outside the range, would trigger an alarm. These parameters are generally measurements taken during treatment, for example, blood pressure, heart rate, body temperature, and change in blood volume.

Another measured parameter is subjective patient comfort. This parameter is not measured by sensors on the hemodialysis machine 102, but rather is input by the patient using the patient comfort feedback mechanism 113. The feedback from the patient can automatically adjust one or more parameters of the treatment, for example the ultrafiltration rate or dialysate temperature. During the prepping stage, the operator (e.g. a clinician, nurse, physician, etc.) sets an acceptable range for the parameter to be adjusted based on the patient comfort feedback mechanism 113. For example, if the patient comfort feedback mechanism is programmed to adjust the ultrafiltration rate, the operator may provide a maximum ultrafiltration rate and a minimum ultrafiltration rate. The blood treatment commences once all parameters have been entered into the hemodialysis machine 102. At this point, the disposable circuit is also primed by flowing a priming fluid through the dialysate lines. The blood treatment begins and fluid is pulled from the blood circuit to the dialysate circuit by the UF pump 180. The UF pump 180 initially operates at an initial UF rate set by the clinician.

If the patient experiences a negative side effect, for example, dizziness, nausea, or cramping, the patient indicates that discomfort using the patient comfort feedback mechanism 113. As the patient uses the patient comfort feedback mechanism 113, the adjustable parameter (e.g., UF rate) may increase or decrease. The provided range ensures that the patient comfort feedback mechanism 113 does not excessively lower or raise the adjustable parameter. In response to this input, the hemodialysis machine 102 reduces the UF rate to remove fluid from the body at a slower pace. This slower pace can reduce the negative side effects but results in a longer total treatment time. The patient is then notified of the new treatment time through the user interface 112. If the patient is comfortable, the patient can indicate that the discomfort is eliminated or reduced by the patient comfort feedback mechanism 113. If the patient indicates an increased comfort level, the machine, in response to the input, increases the UF rate. The increased UF rate results in a shorter treatment time. The patient is notified of the new treatment time through the user interface 112. The patient can indicate discomfort at any point in blood treatment. When the treatment time expires, the blood treatment is complete.

In some cases, the UF rate is greater than or equal to 0.01 ml/hr/kg and is less than or equal to 13 ml/hr/kg. A typical UF rate is within a range of 0.1 ml/hr to 4000 ml/hr (6-8 ml/hr/kg) with an average rate of 1000 ml/hr (where the patient has three liters of fluid to remove over the course of a treatment).

Figure 2:
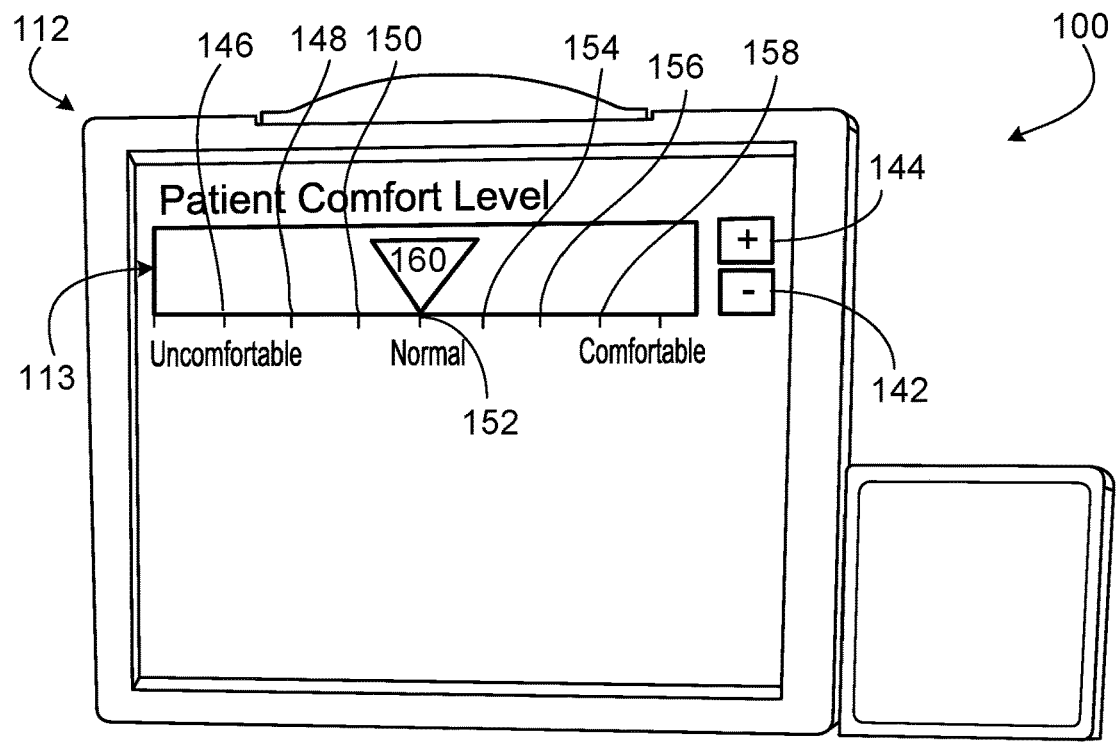
FIG. 2 is an enlarged view of the user interface with the patient comfort feedback mechanism of FIG. 1A.

FIG. 2 is a view of the user interface 112 with the patient comfort feedback mechanism 113. The user interface 112 can display multiple different screens that can be selected by the operator. The screen shown on the user interface 112 in FIG. 2 displays the patient comfort feedback mechanism 113 that can receive patient input regarding their comfort levels using the first input (minus input 142) and the second input (plus input 144) on the user interface 112. As discussed previously, the patient may experience a variety of side effect of the treatment including nausea, tiredness, dizziness, body temperature irregularity, and cramping. These side effects can be mitigated by adjusting parameters of the treatment. In FIG. 2, the adjusted parameter is the ultrafiltration rate.

When the patient experiences discomfort, the patient indicates his/her discomfort by pressing the minus input 142 on the user interface 112. In response to the patient's indicated discomfort, the hemodialysis machine 102 will lower the UF rate. The patient comfort feedback mechanism in FIG. 2 has seven notches or set of points 146, 148, 150, 152, 154, 156, 158 and a movable pointer 160 that sits on one of the seven notches 146, 148, 150, 152, 154, 156, 158. The pointer 160 moves based on the patient comfort input. For example, if that patient presses the minus input 142, the pointer 160 moves to the left from notch 152 to notch 150. If the patient presses the plus input 144, the pointer 160 moves to the right from notch 152 to notch 154. The notches 146, 148, 150, 152, 154, 156, 158 indicate patient comfort, with the middle notch 152 being neutral, the far left notch 146 being the most uncomfortable and the far right notch 158 being the most comfortable. As the patient indicates discomfort by pressing the minus input 142, the pointer 160 moves to the left and the hemodialysis machine 102 lowers the UF rate. The UF rate increases when the patient indicates comfort by moving the pointer 160 to the right using the plus input 144.

As the UF rate changes, so does the treatment time. The lower UF rate results in longer treatment times while the higher UF rates result in shorter treatment times. The notches 146, 148, 150, 152, 154, 156, 158 each define a UF rate within the range provided by the operator during setup. The prescription UF rate is associated with the middle notch 152. The minimum UF rate in the provided range is associated with the far left notch 146 and the maximum UF rate in the provided range is associated with the right most notch 158. For example, if the prescribed UF rate is 3000 ml/hr and UF rate range is defined during setup as 2500 ml/hr to 3500 ml/hr, each notch 146, 148, 150, 152, 154, 156, 158 would represent a 142 ml/hr change in UF rate. Some embodiments have smaller or larger changes in UF rate per notch, such as 10 ml/hr, 5 ml/hr, 15 ml/hr, 20 ml/hr, 50 ml/hr, 100 ml/hr, 150 ml/hr, 200 ml/fr, 250 ml/hr, 300 ml/hr, or 350 ml/hr per notch.

The UF rate dictates the rate of fluid removal from the body and from the blood during the dialysis treatment. While a low level of fluid (blood volume) in the body is preferable, removing the fluid from the blood too quickly can result in negative side effects. For example, even when the UF rate is constant, the body typically does not react in a constant manner. Depending on a variety of factors, the change in blood volume over a period of time will differ through a blood treatment. The patient comfort feedback mechanism 113 can be used to adjust treatment parameters, such as UF rate, in a way that increases the patient's overall comfort level throughout the treatment.

Figure 3:
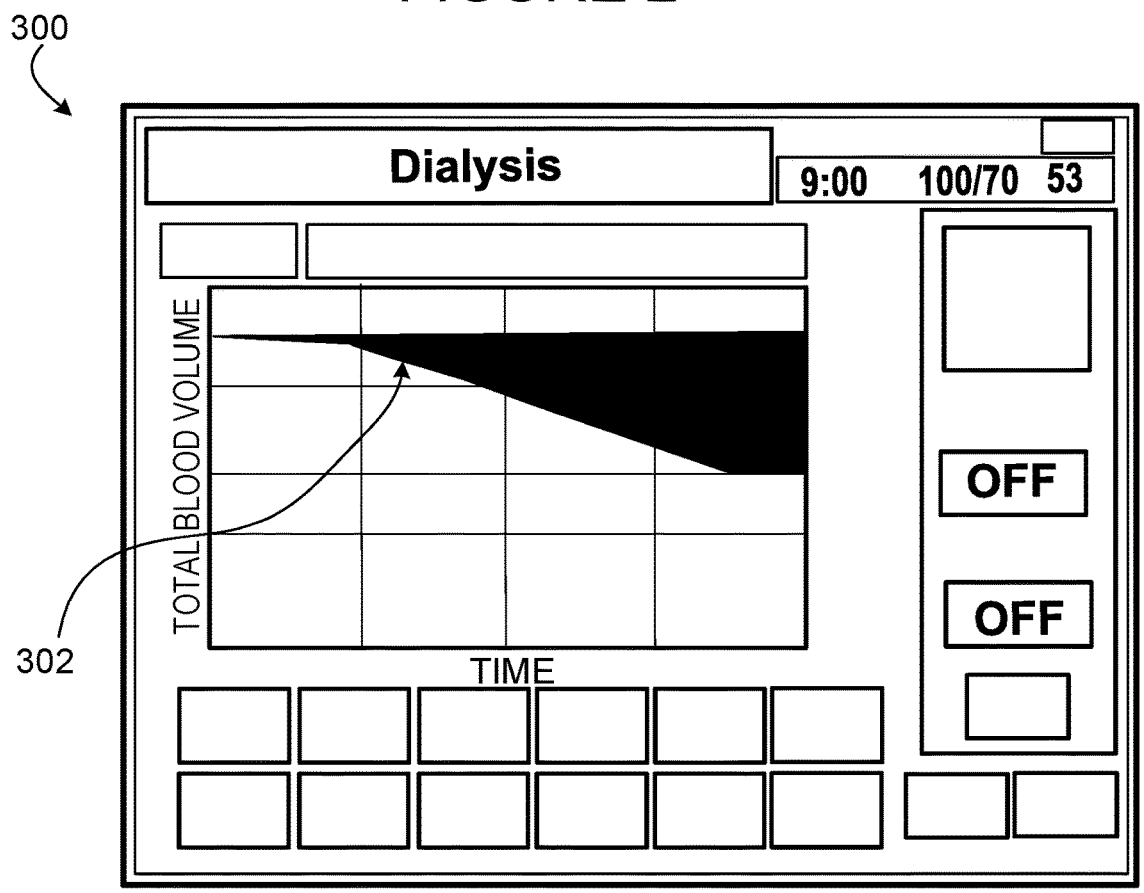
FIG. 3 is a graph on the user interface of FIG. 1A, graphically displaying a blood volume level during a blood treatment.

In addition to the patient feedback mechanism, other information can be displayed for the user b the user interface 112. FIG. 3, for example, shows a graph 300 displayed on the user interface 112, of the percent blood volume line 302 measured continuously during treatment. As discussed above, the percent blood volume can be measured by the crit line 139. The graph 300 is read from left to right, the left being the beginning of blood treatment. The graph 300 shows a treatment in which the UF rate is varied due to patient feedback.

A quick removal of fluid (blood volume) from the body would be shown as a steeply and negatively sloped percent blood volume line 302. An ideal blood volume curve has a steady, low slope going from a high level of fluid to a low level of fluids, as shown in FIG. 3. By including the patient comfort feedback mechanism 113, side effects of the patient can be counteracted by allowing the patient to indicate his/her discomfort on the patient comfort feedback mechanism 113, and decreasing the UF rate before a steep slope occurs. In many cases, the slope of the blood volume curve would maintain a low slope due to the patient comfort feedback mechanism 113 intervention. As a result, the likelihood the patient experiencing negative side effects such as cramps, nausea, and dizziness can be reduced.

Figure 4A:
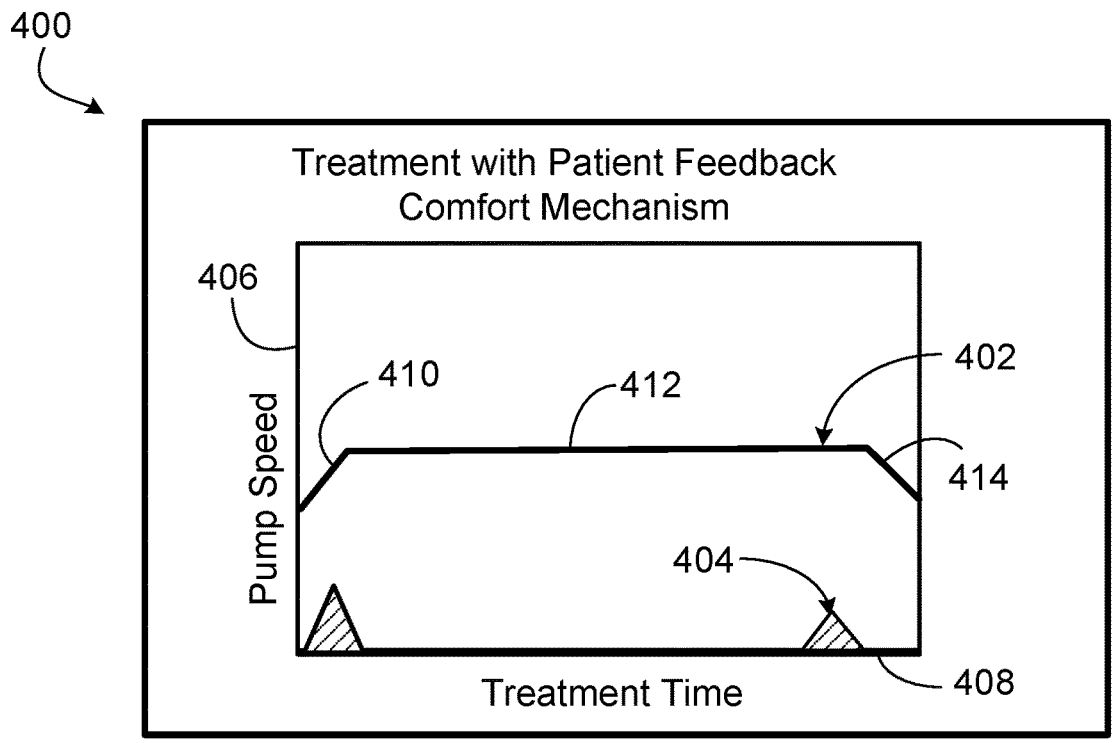
FIGS. 4A and 4B are graphs of ultrafiltration pump rates vs. exemplary patient comfort during treatments.
Figure 4B:
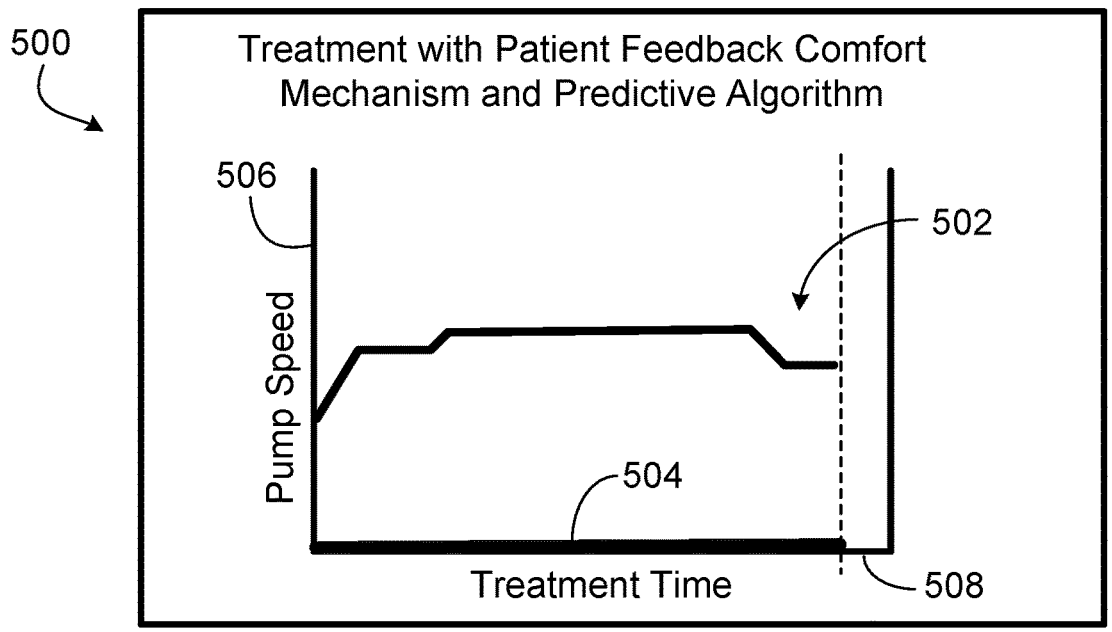

FIGS. 4A and 4B show graphs 400, 500 having a first line 402, 502 that indicates patient comfort and a second line 404, 504 that indicates treatment. The Y-axis 406, 506 represents UF pump speed and the x-axis 408, 508 represents time. FIG. 4A shows a treatment carried out with patient input via the patient comfort feedback mechanism 113. As shown, the UF pump speed varies during treatment, increasing at the beginning of treatment, remaining steady through the middle of treatment, and decreasing at the end of treatment. The beginning of the treatment shows the increase in pump speed in the first sloped section 410. This increase in pump speed is a result of the patient pressing the plus input 144 into the patient comfort feedback mechanism 113. The patient then keeps the mechanism at the same UF rate until the end of treatment. This is shown by the flat section 412. At the end of treatment, the patient experiences discomfort and indicates the discomfort by pressing the minus input 142 on the patient comfort feedback mechanism 113. This decreases the UF rate, shown in the second sloped portion 414. During the entire treatment, the patient discomfort line 404 remains low and the patient experiences very little discomfort.

FIG. 4B shows a treatment line 502 and a patient comfort line 504 on graph 500. In this graph 500, however, the hemodialysis machine 102 of FIG. 1A is equipped with a processor, a memory, and a control unit that includes patient comfort level inputs and treatment data from a variety of patients and treatments. The data set includes a snap shot of the treatment when the patient input was received. The snap shot includes measurements, like blood pressure, temperature, heart rate, sodium profile, UF profile, hematocrit, UF rate, and dialysate temperature. The hemodialysis machine 102 is able to process this data set and identify when the patient will potentially experience discomfort and adjust parameters of the treatment to preemptively mitigate the patient discomfort. The hemodialysis machine 102 does this while also creating the quickest possible treatment with a low level of patient discomfort. When comparing FIG. 4A to 4B, in the simplest iteration, the time of treatment can be seen to be shorter by comparing the point at which the treatment lines 402, 502 stop. This data could be gathered from the previous treatment or aggregated over the course of several treatments. The predictive algorithm could note when the patient discomfort has peaked in the past, e.g., at the two hour mark, and begin a more gentle phase prior to that mark, thereby increasing the time the patient can tolerate a more aggressive treatment. A more advanced version might even, with the physician's input, pursue a slightly more aggressive treatment if the patient has tolerated a certain level consistently during a particular phase and note the differences from the previous standard model it has generated. With this new input, the predictive algorithm may present a more efficient hybrid therapy for additional time-savings. If the predictive algorithm determines that a patient is experiencing dizziness based on the inputs, for example, it may be remedied by a stricter adherence to blood pressure medication: the predictive algorithm could send a notification to the patient by SMS or smartphone or other method to start reminding the patient to take blood pressure medication.

While certain embodiments have been described above, other embodiments are possible.

Figure 5:
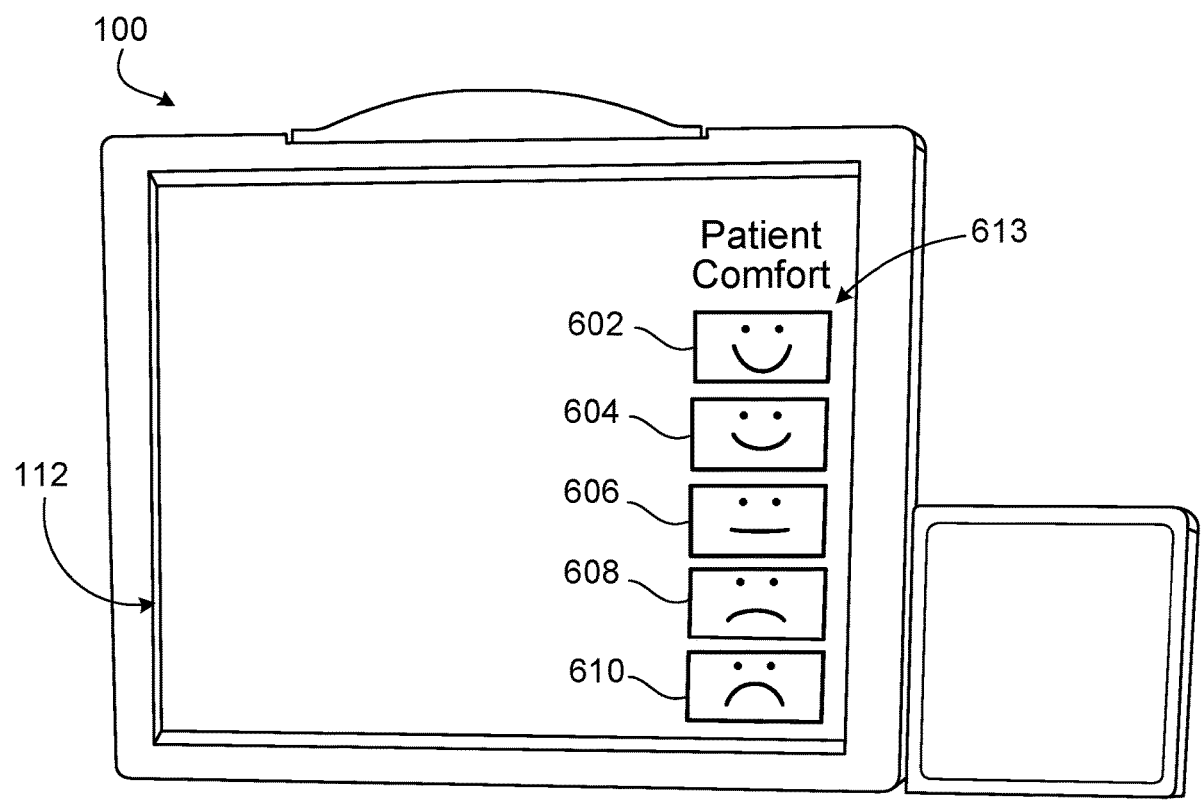
FIG. 5 is another example of the user interface with a patient comfort feedback mechanism having five inputs.

FIG. 5 shows an alternate patient comfort feedback mechanism 613 displayed on the user interface 112. The patient comfort feedback mechanism 613 includes five inputs 602, 604, 606, 608, 610. The first input 602 indicates a high level of patient comfort, the second input 604 indicates a medium level of patient comfort, the third input 606 indicates a neutral level of patient comfort, the fourth input 608 indicates a medium level of patient discomfort, and the fifth input 610 indicates a high level of patient discomfort. The patient is able to touch the input that best reflects his/her comfort level. The first and second inputs 602, 604 indicate a medium to high level of patient comfort and the hemodialysis machine 102 responds accordingly. For example, the hemodialysis machine 102 can automatically increase the UF rate and shorten the treatment time. The third input 606 indicates neutral patient comfort. If the patient touches the third input 606, the UF rate will not change. The fourth and fifth inputs 608, 610 indicate a medium to high level of patient discomfort. In response to a patient touching either the fourth or the fifth input 608, 610, the hemodialysis machine 102 will automatically decrease the UF rate and increase the treatment time. Similar to the patient comfort feedback mechanism 113 discussed in FIG. 2, the rate of UF may drop by a predetermined amount, for example 100 ml/hr from the prescribed UF level. The prescribed UF level is associated with the neutral input 606. The drop in UF rate is determined by the severity of the discomfort. Thus the UF rate may drop by 100 ml/hr (relative to the prescribed rate) when the fourth input 608 (medium discomfort) is touched, and the UF rate may drop by 200 ml/hr (relative to the prescribed rate) when the fifth input 610 (severe discomfort) is touched. The five inputs 602, 604, 606, 608, 610 include icons that visually show the comfort level to the patient. The icons may be colored to further differentiate the representative comfort levels.

In some embodiments, the patient comfort feedback mechanism 613 has more than five inputs or less than five inputs. For example, the patient comfort feedback mechanisms may have two, three, four, six, seven, eight, or nine inputs.

While certain information has been described as being displayed via the user interface 112, other types of devices can be used to allow user interaction with the dialysis machine. For example, in some implementations, the hemodialysis machine includes a user interface having traditional screen (i.e., a non-touch screen) along with a separate device, such as a keyboard, for inputting data. Alternatively or additionally, the hemodialysis machine can be equipped with a scratch pad and/or touch buttons that permit the operator to input data.

Figure 6:
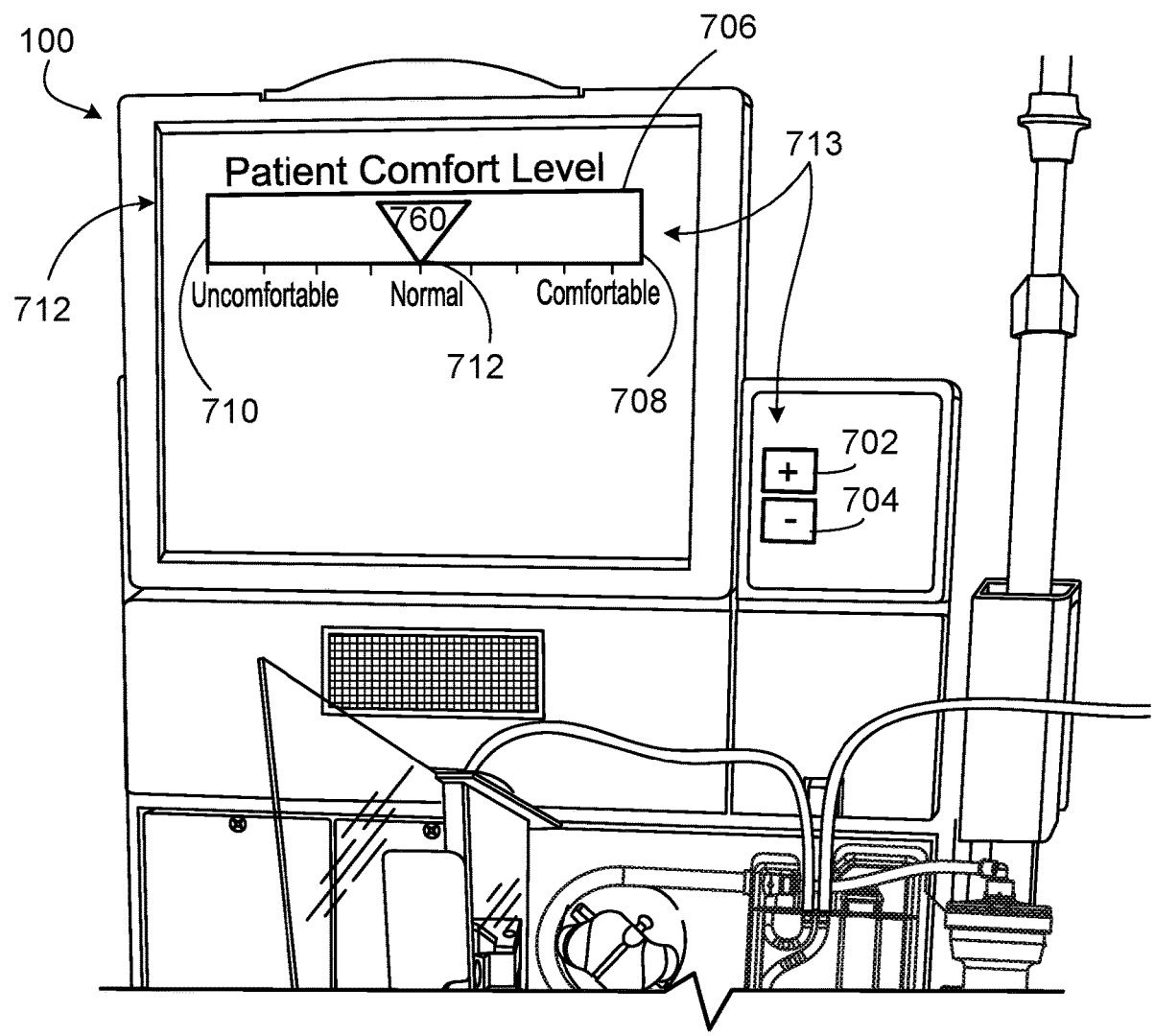
FIG. 6 illustrates a mechanical patient comfort feedback mechanism with buttons that control a display on the user interface and a parameter of blood treatment.

FIG. 6 shows a display of a user interface 712 and a patient comfort feedback mechanism 713 compatible with the hemodialysis machine 102. The user interface 712 is similar to user interface 112, however, user interface 712 is not a touchscreen. The patient comfort feedback mechanism 713 includes a first button 702 mounted on the hemodialysis machine 102 and a second button 704 mounted on the hemodialysis machine 102. The first and second buttons 702, 704 change the patient comfort level when pressed. The changes in patient comfort level are shown on the patient comfort level bar 706 displayed on the user interface 712. The level of patient comfort is indicated by a pointer 760, in a similar manner to the pointed described in FIG. 2. The pointer 760 moves along the bar 706 when the first or second button 702, 704 is pressed. The first button 702 shows a plus and when pressed, indicates increased patient comfort. The pointer 760 the moves to the right on the bar 706, towards the comfortable level 708. The second button 704 shows a minus sign and when pressed, indicates a decrease in patient comfort level. The pointer 760 moves to the left on the bar 706, towards the uncomfortable level 710. The bar 706 in FIG. 6 shows three levels of patient comfort: comfortable (level 708), uncomfortable (level 710), and normal (level 714). Each level is associated with a predetermined UF rate. The comfortable level 708 has a higher UF rate than both the normal and uncomfortable levels 714, 710. The UF rate associated with the uncomfortable level 710 is lower than the UF rate associated with the normal level 714 and the UF rate associated with the comfortable level 708. In some embodiments, the UF rates change by a factor of 100 ml/hr per level. In other embodiments, the UF rates change by a factor larger or smaller than 100 ml/hr, for example 10 ml/hr or 30 ml/hr. Additionally, some embodiments may have additional comfort levels to more specifically gage the patient's comfort. The UF rate then can change by a smaller factor, allowing a more specific UF rate to be chosen, rather than a UF rate within a multiple of 10 ml/hr. Once the pointer 760 is at the comfortable level 708, at the right edge of the bar 706, the first button 702 will not be recognized. At this point on the bar 706, the patient comfort level is maxed out. The patient may still press the first button 702, but the pointer 760 and UF rate will not change.

Figure 7:
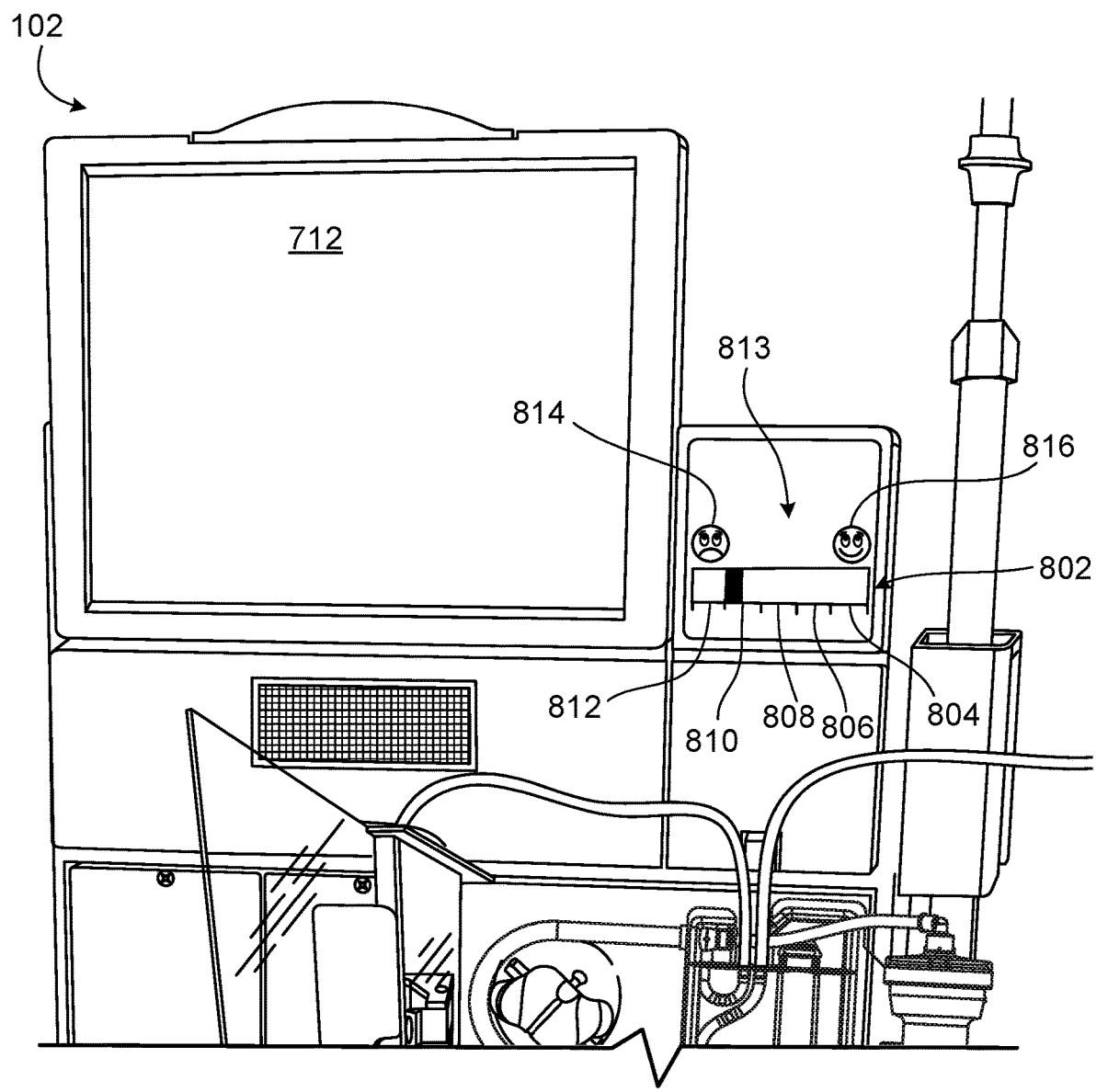
FIG. 7 is a view of a mechanical patient comfort feedback mechanism including a dial mounted on a face of the blood treatment machine.

FIG. 7 shows a patient comfort feedback mechanism 813 mounted on the hemodialysis machine 102. The patient comfort feedback mechanism 813 includes a slider 802 with five levels 804, 806, 808, 810, 812 of patient comfort, separated by dashes. The far right level 804 indicates a high level of patient comfort and the far left level 812 indicates a high level of patient discomfort. The middle level 808 indicates a neutral patient comfort. A discomfort icon 814 and a comfort icon 816 show the patient which side of the slider represents discomfort and which side of the slider represents comfort. As the patient experiences discomfort, the patient will move the slider to the left, towards the discomfort icon 814. The UF rate will decrease in response to the patient input, by a factor of 100 ml/hr for the first left level 810 and another factor of 100 ml/hr for the second left level 812. The treatment time is increased due to the decrease in UF rate. As the patient begins to feel better, he/she will move the slider to the right, towards the comfort icon 816, to indicate his/her new level of comfort. If the patient moves the slider from the second left level 812 position to the first left level 810, the UF rate increases by 100 ml/hr but remains 100 ml/hr below the prescribed level. If the operator moves the slider to the middle level 808, the UF rate returns to the prescribed amount. If the patient moves the slider to the first right level 806, the UF rate increases by 100 ml/hr. This would also decrease the amount of treatment time. Moving the slider to the second right level 804 increases the UF rate further by 100 ml/hr and decreases the treatment time.

Figure 8:
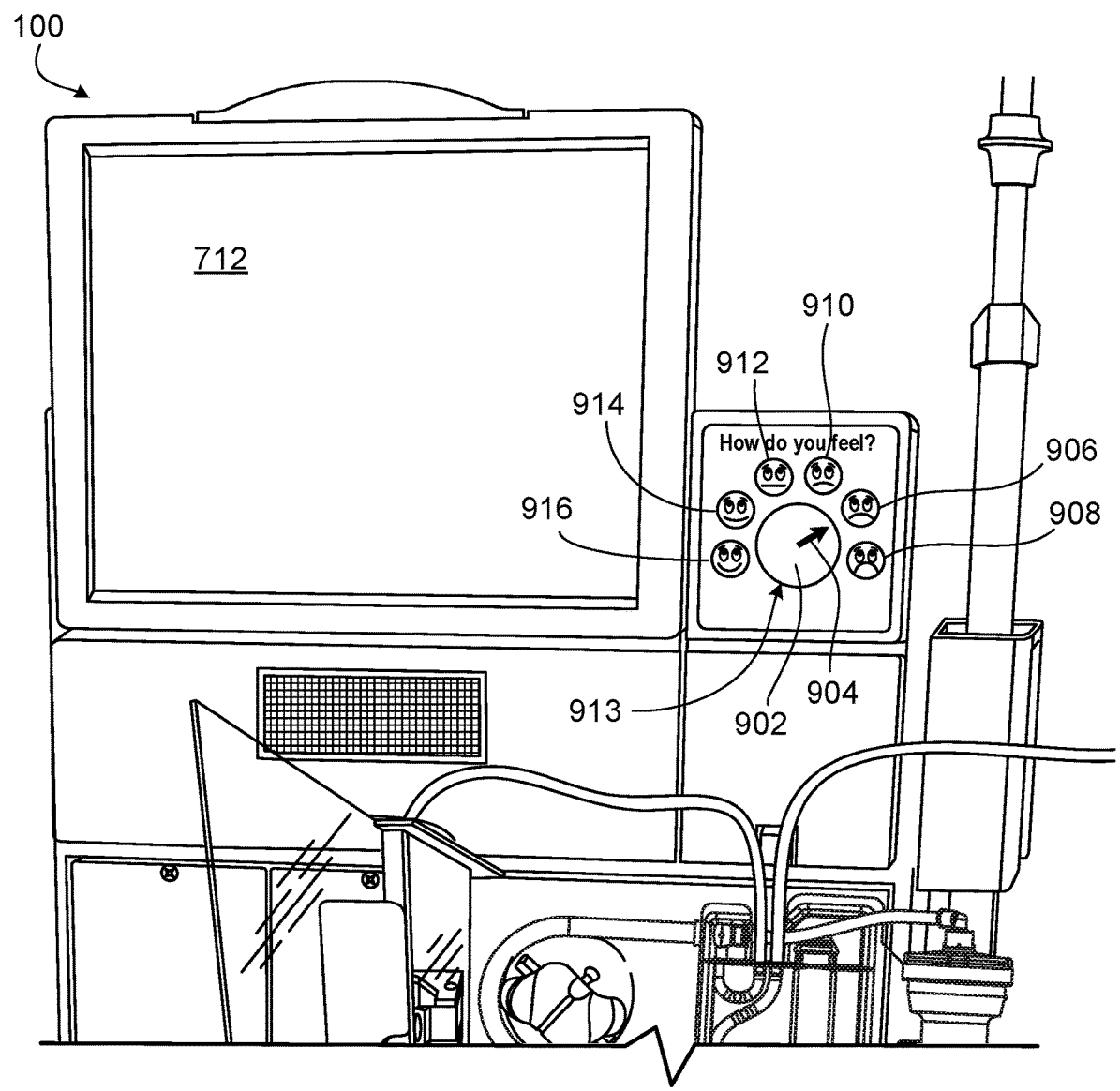
FIG. 8 is a view of a mechanical patient comfort feedback mechanism including a slider mounted on a face of the blood treatment machine.

FIG. 8 shows a patient comfort feedback mechanism 913 mounted on the hemodialysis machine 102. The operator feedback mechanism includes a rotatable dial 902 with icon indicators that indicate patient comfort levels. The dial 902 includes an arrow 904 that points to an icon indicator 906. When the arrow 904 points to the icon 906, the icon indicator 906 that is pointed at is registered as the patient comfort level by the hemodialysis machine 102. FIG. 8 shows six different icon indicators 906, 908, 910, 912, 914, 916. The UF rate changes based on which icon indicator 906, 908, 910, 912, 914, 916 is pointed to. For example if the arrow 904 points to the right most icon indicator 909, the patient is experiencing a high level of discomfort and the UF rate is decreased to a predetermined value. In some embodiment, each icon indicator 906, 908, 910, 912, 914, 916 indicates a change of 100 ml/hr from the prescribed UF rate. In the example discussed previously, the right most icon indicator 908 would decrease the prescribed UF rate by ml/hr. Some embodiments may have a lower or higher rate of increase/decrease, for example, 50 ml/hr 150 ml/hr, or 300 ml/hr. The decrease in UF rate also increase the treatment time.

Figure 9:
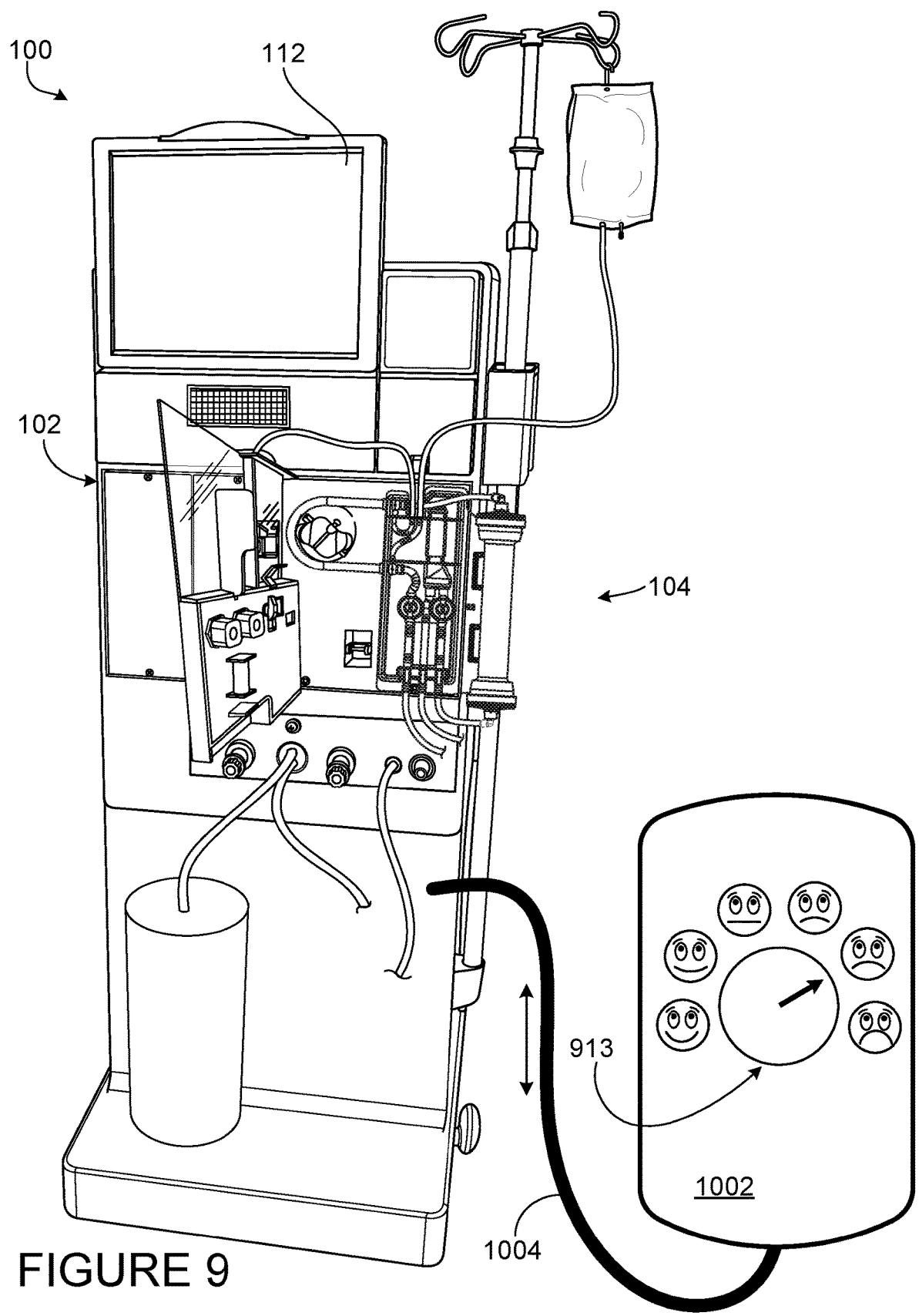
FIG. 9 is a view of a mechanical patient comfort feedback mechanism including a dial mounted on a face of a wired remote of the blood treatment machine.

FIG. 9 shows a patient comfort feedback mechanism 1013 that is similar to patient comfort feedback mechanism 913 of FIG. 8 mounted on a remote control 1002. The remote is 1002 wired to the hemodialysis machine 102 using wire 1004. The patient comfort feedback mechanism 1013 operates in the same way as patient comfort feedback mechanism 913. Mounting the patient comfort feedback mechanism 913 to the remote control 1002 can reduce patient movement, particularly if the patient is seated by reducing the need to reach for the hemodialysis machine 102 to adjust the patient comfort level.

In some embodiments the remote control 1002 is wirelessly connected to the hemodialysis machine 102. In such embodiments, the hemodialysis machine 102 and the remote control 1002 both include signal transceivers that are operable to send signals to and receive signals from each other.

Figure 10:
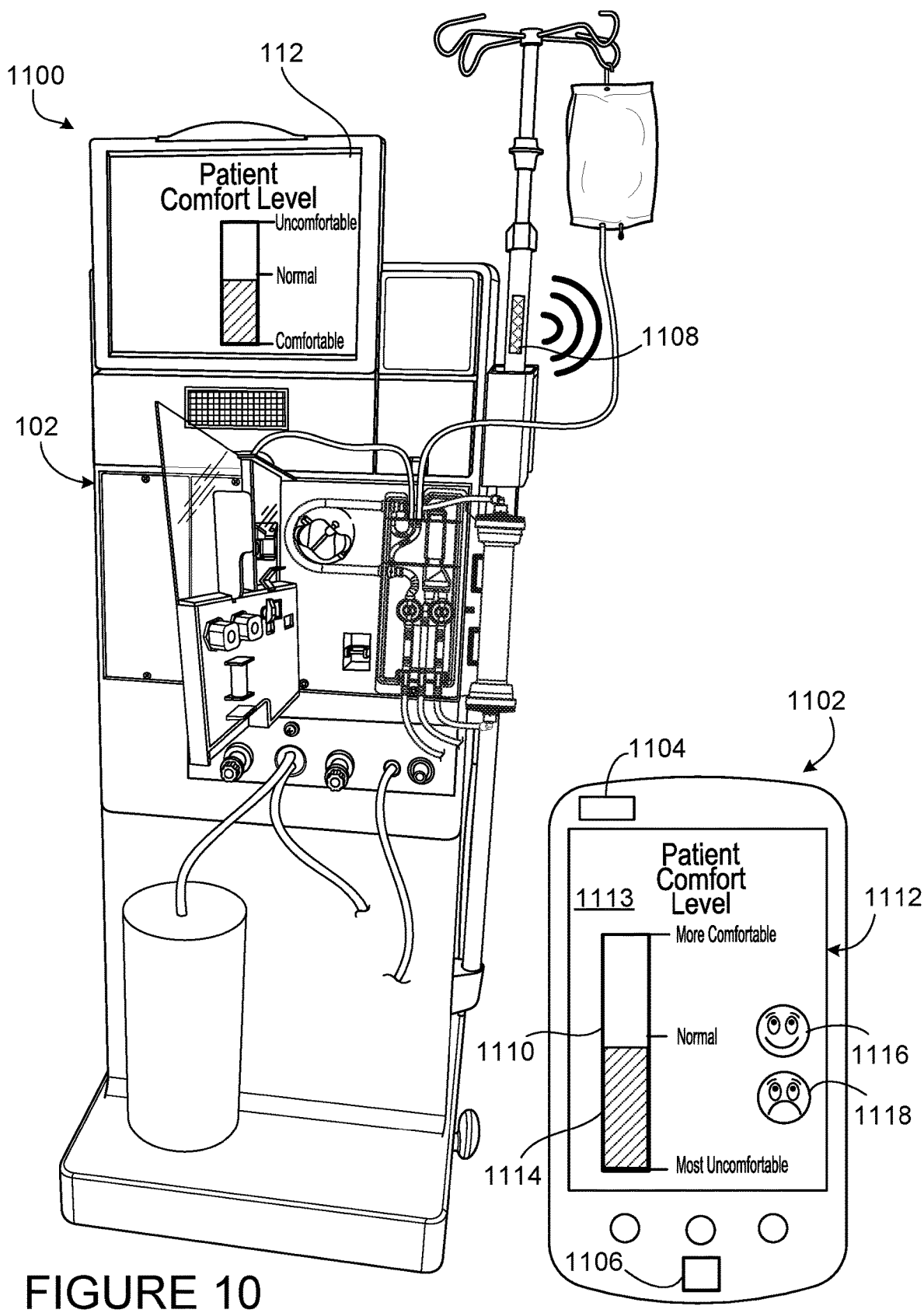
FIG. 10 illustrates a blood treatment machine that is wirelessly connected to a mobile computing device that includes a patient comfort feedback mechanism.

FIG. 10 shows a blood treatment system 1100 including a hemodialysis machine 102 and a portable device (e.g., a smart phone) 1102. The smart phone 1102 includes a user interface 1112, a signal transceiver 1104, and a processor 1106. The user interface 1112 is a touch screen and displays a patient comfort feedback mechanism 1113. The smart phone 1102 is wirelessly connected to the hemodialysis machine 102 and is operable to send and receive patient comfort data to the hemodialysis machine 102 using the signal transceiver 1104. The hemodialysis machine 102 includes a signal transceiver 1108 to send and receive patient comfort data from the smart phone 1102. The patient comfort feedback mechanism 1113 is an app that is downloadable onto the smart phone 1102. When the app is opened, the user interface 1112 displays the patient comfort feedback mechanism 1113. The patient comfort feedback mechanism 1113 includes a vertical bar 1110 with ten levels, defined by nine dashes. The current patient comfort level is shown via the shaded bar 1114 The patient comfort feedback mechanism 1113 also includes a comfort input 1116 and a discomfort input 1118. The comfort input 1116 has a smiley face icon and the discomfort input 1118 has a sad faced icon. The patient is shown as experiencing slight discomfort, indicated by the shaded bar 1114 being slightly below a normal level 1120. The treatment begins at the normal level 1120, therefore the patient has pressed the discomfort input 1118 one time. The shaded bar 1114 then moves downward, so that instead of extending to the normal level 1120, the shaded bar extends to a second lower level 1122, in the discomfort direction. The hemodialysis machine 102 responds by slightly decreasing the UF rate, for example by 100 ml/hr or 200 ml/hr. The treatment time is increased when the UF rate is decreased. The user interface 1112 may notify the patient that the treatment time will increase. In some embodiments, an estimated treatment time can be displayed on the user interface 1112.

While certain embodiments have been described in which the UF rate is adjusted by a particular amount in response to the patient adjusting the patient feedback mechanism, it should be appreciated that the dialysis machines can be configured to adjust the UF rate by any suitable amount in response to input at the patient feedback mechanism. Additionally, the interval value between UF rates on various patient comfort feedback mechanisms may be larger or smaller than those described above.

In addition, while the dialysis machines above have been described as being configured to adjust the UF in response to input at the patient feedback mechanism, the dialysis machines can alternatively or additionally be configured to adjust one or more other treatment parameters in response to input at the patient feedback mechanism.

Figure 11:
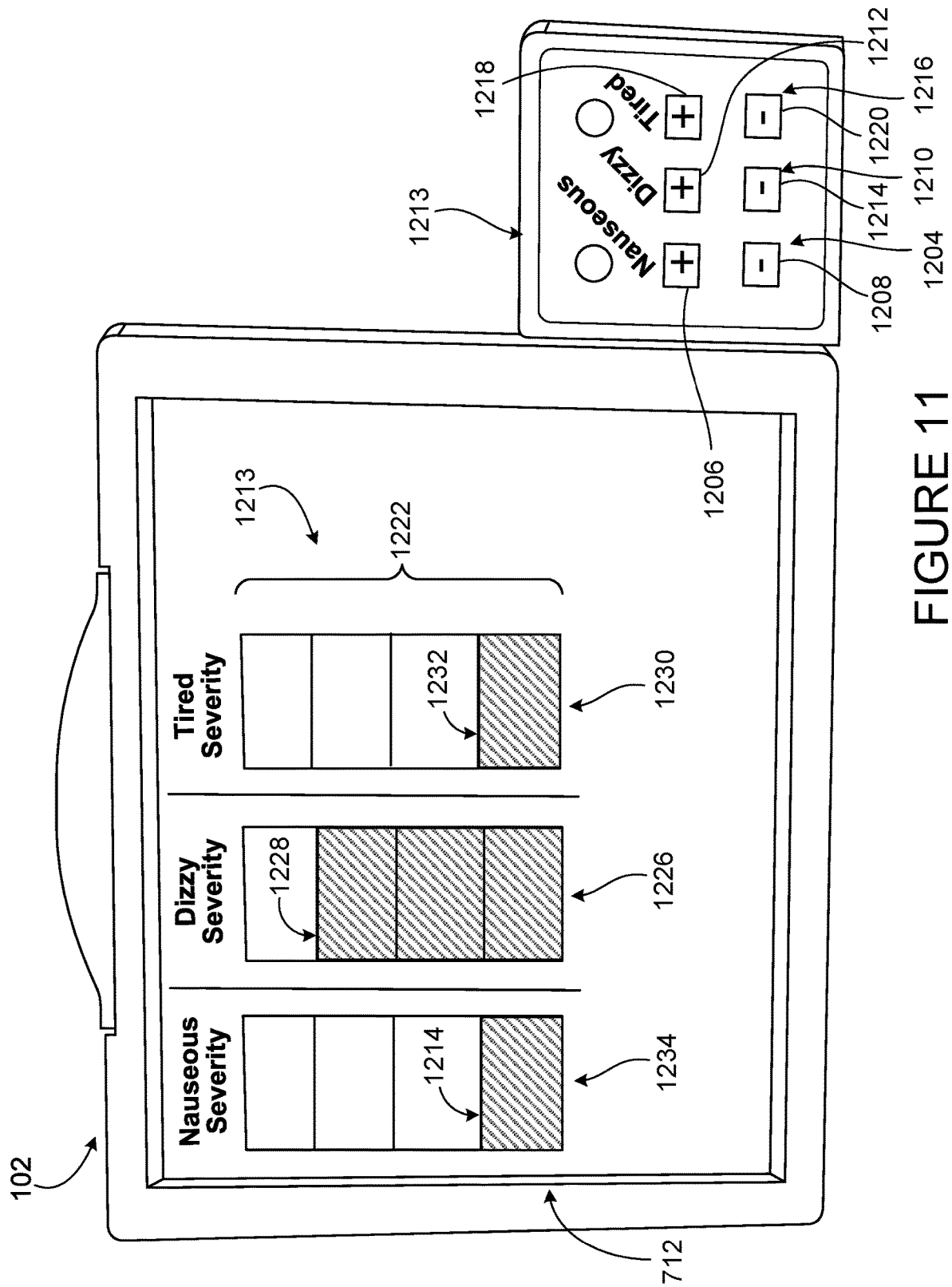
FIG. 11 is a view of a mechanical patient feedback mechanism with sets of buttons that permit patient input related to three predetermined patient conditions or sensations.

FIG. 11 shows a hemodialysis machine with a patient comfort feedback mechanism 1213. The patient comfort feedback mechanism 1213 includes six buttons that are associated with common side effects of dialysis. A first set of buttons 1204 includes a first button 1206 and a second button 1208 and can be used to indicate that the patient is experiencing nausea. A second of buttons 1210 includes a third button 1212 and a fourth button 1214 and can be used to indicate that the patient is experiencing dizziness A third set of buttons 1216 includes a fourth button 1214 and a fifth button 1218 and can be used to indicate that the patient is experiencing tiredness. Each set of buttons 1204, 1210, 1216 is associated with a bar on the display. The first bar 1222 shows a nausea level 1224, the second bar 1226 shows a dizziness level 1228, and a third bar 1230 shows a tiredness level 1232. Some systems have additional bars, for example a fourth bar for cramping and a fifth bar for headaches. The patient may adjust each side effect differently as opposed to just indicating discomfort. As explained above, the hemodialysis machine 102 has a variety of parameters than can be adjusted. In the patient comfort feedback mechanism 1213, each side effect is addressed by adjusting one or more parameters. For example, indicating a level of nausea adjusts at least one of the ultrafiltration rate, a sodium level, and a dialysate flow rate. Some systems generate a notification reminding patient to drink less fluid in response to a patient input indicating nausea. Indicating a level of dizziness adjusts at least one the ultrafiltration rate, the sodium level, and a saline infusion rate. Some systems generate a notification reminding patient to take blood pressure medication in response to a patient input indicating dizziness. Indicating a level of tiredness adjusts at least one of the treatment time and dialysate temperature. Some systems generate a notification reminding patient to move his/her limbs to a patient input indicating tiredness or fatigue.

As mentioned previously, other system may include a bar and button inputs that display and adjust levels of cramping or headaches. Indicating a level of cramping adjusts at least one of the ultrafiltration rate, the treatment time, calcium levels, the saline infusion rate, and the dialysate flow rate. Some systems generate a notification reminding patient to move his/her limbs to a patient input indicating cramping. Indicating a level of headaches adjusts at least one of the treatment time, the number of periodic blood pressure measurements during treatment, and the sodium level.

The first 1222 bar has five levels that can be adjusted by using the first set of buttons 1204. The first button 1206 has a plus sign and the second button 1208 has a minus sign. The patient presses the first button 1206 when they experience nausea. For each press of the first button 1206 the nausea level 1224 increases. Originally, the nausea level 1224 is at zero 1234 and the first bar 1222 is completely unshaded. Pressing the first button 1204 once increases the nausea level 1224 to a low level, as shown in FIG. 11. Pressing the first button 1206 again will result in the nausea level 1224 increases to medium. Pressing the first button 1206 a third time will increase the nausea level 1224 to high and pressing the first button 1204 a fourth time will increase the nausea level 1224 to severe. When the nausea level 1224 is severe, the first bar 1222 is fully shaded. The first button 1206 and second button 1208 adjust the ultrafiltration rate, a sodium level, or a dialysate flow rate at a predetermined rate based on the level of nausea indicated by the patient.

The third button 1212 has a plus icon and the fourth button 1214 has a minus icon. Pressing the third button 1212 increases the displayed dizziness level 1228 shown on the second bar 1226 and the fourth button 1214 decreases the displayed dizziness level 1228. As the third button 1212 is pressed the second bar 1226, which is initially unshaded, becomes increasingly shaded. As displayed in FIG. 11, the second bar 1226 is at a high level. If the patient were to press the third button 1212 again, the level of the second bar 1226 would be fully shaded and the dizziness level 1228 would be set to severe. The second set of buttons 1210 adjusts the blood pump rate. Similar to the first set of buttons 1204, pressing the third button 1212, indicating increased dizziness, results in adjustment of the parameter the ultrafiltration rate, the sodium level, or a saline infusion rate. Initially, the second bar 1226 begins unshaded and is only shaded by the pressing of the third button 1212. The patient may indicate reduced dizziness by pressing the fourth button 1214 and lowering the dizziness level 1228. The third button 1212 and fourth button 1214 adjust the ultrafiltration rate, the sodium level, or a saline infusion rate at a predetermined rate based on the level of dizziness indicated by the patient.

The fifth button 1218 has a plus icon and the sixth button 1220 has a minus icon. The fifth button 1218 increases the tiredness level 1232 and the sixth button 1220 reduces the tiredness level 1232. The tiredness level 1232 is displayed on the user interface 712. The tiredness level 1232 shown on the user interface 712 in FIG. 11, is a result of one press of the fifth button 1218. This is shown by the third bar 1230 being shaded to a low level. The third set of buttons 1216 adjust parameters the treatment time or dialysate temperature. The fifth button 1218 increases the displayed tiredness level 1232 adjusts the parameter (the treatment time or dialysate temperature) while the sixth button 1220 decreases the tiredness level 1232 adjusts the parameter in the opposite way as the fifth button 1218.

Additional sets of buttons and associated bars can be added for additional side effects, for example, perceived body temperature, cramping, and/or itching. In embodiments that include patient feedback for perceived body temperature, the hemodialysis machine can adjust the temperature of the dialysate or the temperature of the blood in the blood chamber. When the patient indicates that he/she feels cold, the machine, in response, increases the temperature of the dialysate or blood. When the patient indicates that he/she feels hot, the machine decreases the temperature of the dialysate or blood.

Some adjustable parameters, such as dialysate temperature do not affect treatment time. Increasing or decreasing the dialysate temperature does not increase or decrease the treatment time.

Additional parameters that can be adjusted based on patient comfort include sodium level, UF profile (various ultrafiltration levels at different times during treatment), infusing saline or other substitution fluid (as part of hemodiafiltration), dialysate flow rate, treatment time, blood flow rate, frequency of blood pressure measurements, and calcium level.

In some blood treatment machines, certain blood components and bloodlines that make up the blood circuit are incorporated into an integrated blood component set. The various components of the integrated blood circuit can be formed together in one assembly or integrated molding rather than discrete separate or modular devices. The integrated blood component set can be adapted to removably seat into the module of the blood treatment machine in a manner similar to the blood component set 104 described with reference to FIG. 1.

While the various blood components are either secured to a carrier body or incorporated into an integrated blood component set 104, the blood components can alternatively be connected to one another by bloodlines alone. In such implementations, the blood components would be individually secured to the blood treatment machine (e.g., the module 124 of the hemodialysis machine 102) prior to treatment. The functionality of the blood components would be similar to the functionality of those blood components discussed with reference to FIG. 1.

While the dialysate circuit has been described as being partially integrated with the hemodialysis machine 102, the dialysate circuit can alternatively be formed by a dialysate component set that can be removably secured to a blood treatment machine during use. In some implementations, the dialysate component set is in the form of a cassette that can be inserted into a drawer of the blood treatment machine in a manner such that the cassette operatively engages components of the blood treatment machine when the drawer is closed. Such a dialysate component sets is described, for example, in U.S. Pat. No. 9,526,820, entitled "Dialysis Systems, Components, and Methods," which is incorporated by reference herein.

While the patient feedback mechanisms described above have been described as being part of hemodialysis machines, similar patient feedback mechanisms can be incorporated into any of various other blood treatment machines, including hemofiltration machines, hemofiltration machines, and peritoneal dialysis machines.

Figure 12:
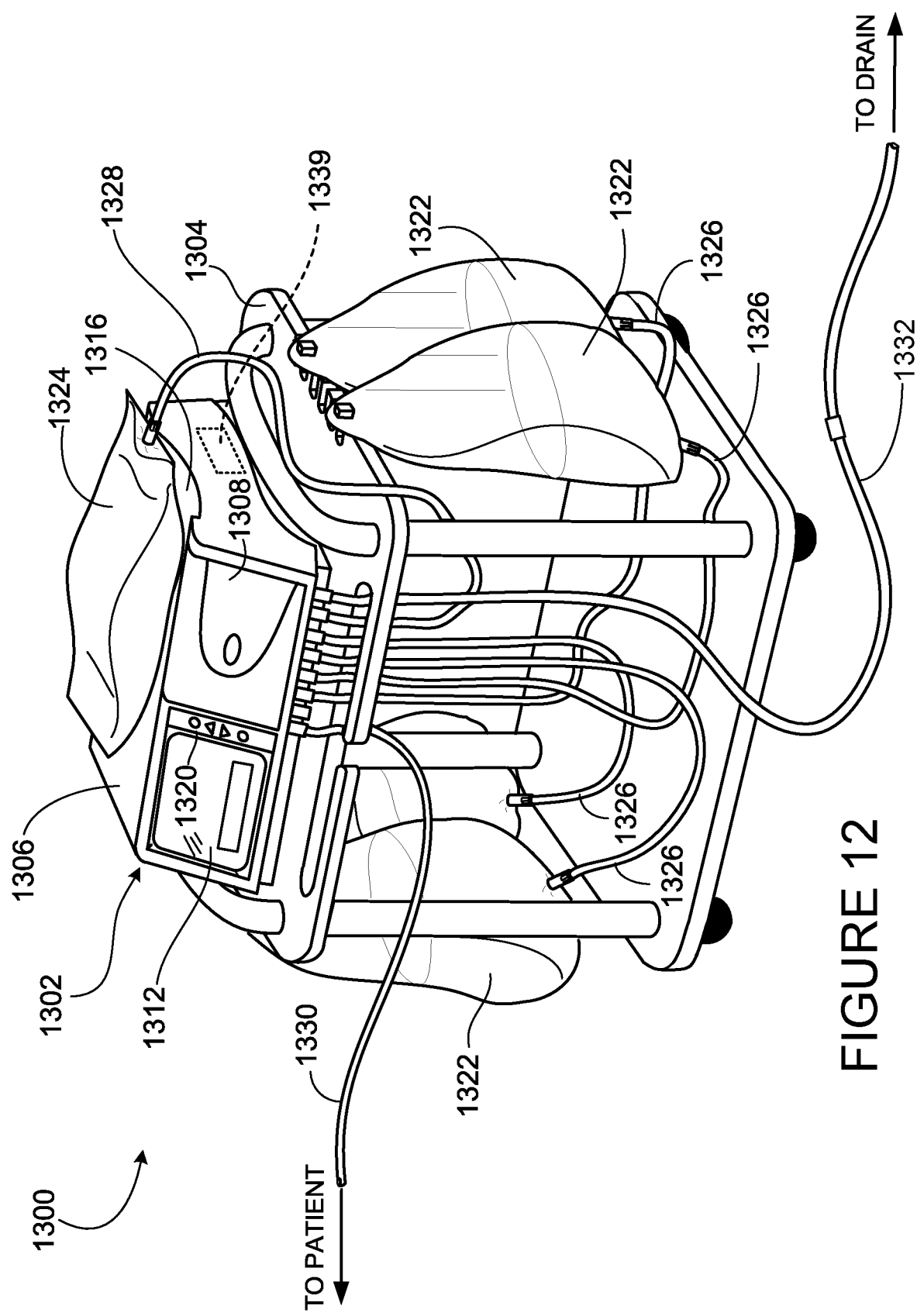
FIG. 12 is a view of a peritoneal dialysis machine with a patient comfort feedback mechanism.
Figure 13:
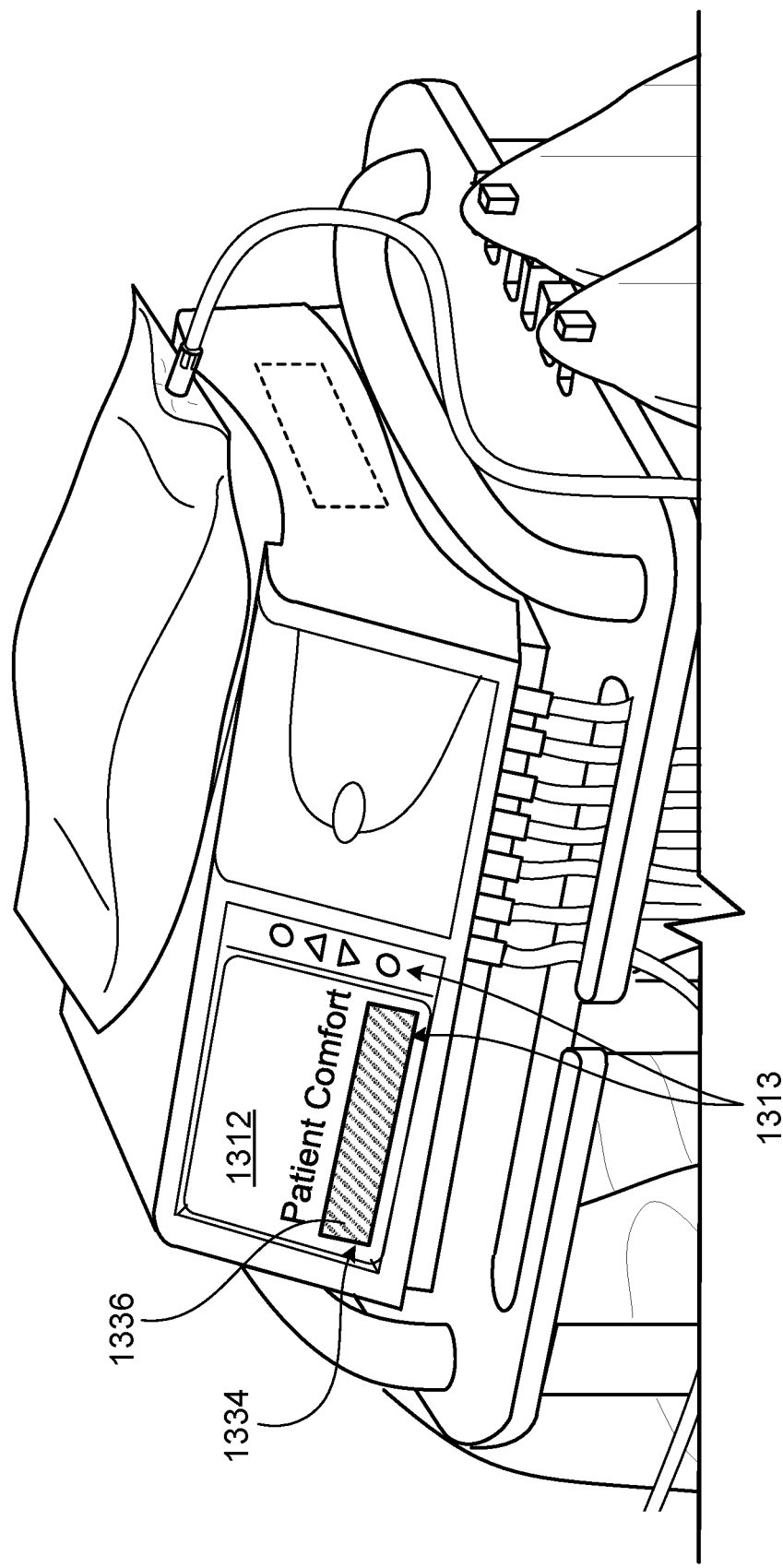
FIG. 13 is a view of the patient comfort feedback mechanism shown in FIG. 12.

FIG. 12 shows a peritoneal dialysis (PD) system 1300 that includes a PD cycler 1302 (also referred to as a PD machine 1302) seated on a cart 1304. Referring also to FIG. 13, the PD cycler 1302 includes a housing 1306, a door 1308, and a cassette interface that contacts a disposable PD cassette when the cassette is disposed within a cassette compartment formed between the cassette interface and the closed door. A heater tray 1316 is positioned on top of the housing 1306. The heater tray 1316 is sized and shaped to accommodate a bag of dialysate 1322 (e.g., a 5 liter bag of dialysate). The PD cycler 1302 also includes a touch screen 1312 and additional control buttons 1320 that can be operated by an operator (e.g., a patient) to allow, for example, set-up, initiation, and/or termination of a PD treatment. The buttons 1320 and touch screen 1312 can also be used as a patient comfort feedback mechanism 1313.

Dialysate bags 1322 are suspended from fingers on the sides of the cart 1304, and a heater bag 1324 is positioned in the heater tray 1316. The dialysate bags 1322 and the heater bag 1324 are connected to the cassette via dialysate bag lines 1326 and a heater bag line 1328, respectively. The dialysate bag lines 1326 can be used to pass dialysate from dialysate bags 1322 to the cassette during use, and the heater bag line 1328 can be used to pass dialysate back and forth between the cassette and the heater bag 1324 during use. In addition, a patient line 1330 and a drain line 1332 are connected to the cassette. The patient line 1330 can be connected to a patient's abdomen via a catheter and can be used to pass dialysate back and forth between the cassette and the patient's peritoneal cavity during use. The drain line 1332 can be connected to a drain or drain receptacle and can be used to pass spent dialysate (e.g., dialysate withdrawn from the patient's peritoneal cavity through the patient line 1330) from the cassette to the drain or drain receptacle during use. The spent dialysate is also referred to as effluent herein. The drain line 1332 is equipped with a chemical testing device that can be used to analyze the effluent to detect signs of infection of the patient's peritoneum.

FIG. 13 shows an enlarged view of the patient comfort feedback mechanism 1313. The touch screen 1312 displays a patient comfort bar 1334 that includes a shaded portion 1336 that indicates the patient comfort. The shaded portion 1336 is controlled by the buttons 1320. The buttons 1320 include a first button 1338 that increases the shaded portion 1336 within the patient comfort bar 1334 and a second button 1340 that decreases the shaded portion 1336 in the patient comfort bar 1334. The first button 1338 is pressed to indicate that the patient is uncomfortable. The machine responds to the discomfort input (pressing of the first button 1338) by adjusting a parameter of the PD system 1300 and increasing the shaded portion 1336 of the patient comfort bar 1334. The second button 1340 is pressed to indicate that the patient is comfortable. The machine responds to the comfort input (pressing of the second button 1340) by adjusting the parameter of the PD system 1300 and decreasing the shaded portion 1336 of the patient comfort bar 1334. If the machine increases the parameter after the patient presses the first button, the machine decreases the parameter after the patient presses the second button. Alternatively, if the machine decreases the parameter after the patient presses the first button, the machine increases the parameter after the patient presses the second button.

The patient comfort feedback mechanism in a PD machine may change a variety of parameters, including dialysate temperature, dwell time, concentration of sodium, and concentration of dextrose.

Any of the various different patient comfort feedback mechanisms described above can also be used with the peritoneal dialysis system 1300.

A number of embodiments of the invention have been described. Nevertheless, it will be understood that various modifications may be made without departing from the spirit and scope of the invention. Accordingly, other embodiments are within the scope of the following claims.

What is claimed is:

1. A blood treatment machine comprising:
    a patient comfort feedback mechanism configured to be adjusted by a patient to select a level of severity of at least one negative side effect of blood treatment currently being experienced by the patient and to generate patient feedback data representing the level of severity of the at least one negative side effect of blood treatment selected by the patient, the at least one negative side effect of blood treatment comprising at least one of nausea, tiredness, dizziness, body temperature irregularity, cramping, itching, or headaches,
    an ultrafiltration adjustment mechanism configured to adjust an ultrafiltration rate, and
    a signal transceiver configured to send the patient feedback data to a controller of the blood treatment machine, the controller configured to receive the patient feedback data from the signal transceiver and adjust a treatment parameter based on the level of severity of the at least one negative side effect of blood treatment selected by the patient, wherein the treatment parameter is at least one of: a sodium level, an ultrafiltration rate, a saline infusion rate, a dialysate flow rate, a treatment time, a blood flow rate, a frequency of blood pressure measurements, a calcium level, a pump rate, a drain percentage, a dialysate dwell time, and fluid temperatures.

2. The blood treatment machine according to claim 1, wherein the treatment parameter is the ultrafiltration rate.

3. The blood treatment machine according to claim 2, wherein the controller lowers the ultrafiltration rate in response to the level of severity of the at least one negative side effect of blood treatment selected by the patient.

4. The blood treatment machine according to claim 1, wherein the blood treatment machine comprises a user interface, controlled by the controller.

5. The blood treatment machine according to claim 4, wherein the controller displays the patient feedback data on the user interface of the blood treatment machine.

6. The blood treatment machine according to claim 5, wherein the patient comfort feedback mechanism is adjusted using a mechanical input on the blood treatment machine.

7. The blood treatment machine according to claim 4, wherein the user interface is a touchscreen.

8. The blood treatment machine according to claim 7, wherein the patient comfort feedback mechanism is adjusted using inputs on the touchscreen.

9. The blood treatment machine according to claim 1, wherein the patient comfort feedback mechanism is adjusted using a mechanical input on the blood treatment machine.

10. The blood treatment machine according to claim 9, wherein the mechanical input is at least one of two buttons, a slider, or a dial.

11. The blood treatment machine according to claim 1, wherein the patient comfort feedback mechanism is a mechanical input mounted on a housing of the blood treatment machine.

12. The blood treatment machine according to claim 11, wherein the mechanical input is at least one of two buttons, a slider, and a dial.

13. The blood treatment machine according to claim 1, wherein the patient comfort feedback mechanism includes icons that correspond to levels of severity of the at least one negative side effect of blood treatment.

14. The blood treatment machine according to claim 1, wherein the patient comfort feedback mechanism is mounted on a body connected to the blood treatment machine by a wire.

15. The blood treatment machine according to claim 1, wherein the patient comfort feedback mechanism provides at least three levels of severity of the at least one negative side effect of blood treatment.

16. The blood treatment machine according to claim 1, wherein the blood treatment machine is a hemodialysis machine.

17. The blood treatment machine according to claim 1, wherein the blood treatment machine is a peritoneal dialysis machine.

18. The blood treatment machine according to claim 1, wherein the controller is configured to adjust the treatment parameter to a predetermined level corresponding to the level of severity of the at least one negative side effect of blood treatment selected by the patient.

19. A system for blood treatment comprising:
a blood treatment machine comprising:
  a signal transceiver configured to send and receive signals,
  a controller configured to control the blood treatment machine and adjust a treatment parameter based on a level of severity of at least one negative side effect of blood treatment selected by a patient, wherein the treatment parameter is at least one of: a sodium level, an ultrafiltration rate, a saline infusion rate, a dialysate flow rate, a treatment time, a blood flow rate, a frequency of blood pressure measurements, a calcium level, a pump rate, a drain percentage, a dialysate dwell time, and fluid temperatures; and
  an ultrafiltration adjustment mechanism configured to adjust the ultrafiltration rate; and
a patient comfort feedback mechanism connected to the blood treatment machine, the patient comfort feedback mechanism comprising:
  a patient configured to be adjusted by a patient to select the level of severity of the at least one negative side effect of blood treatment currently being experienced by the patient and to generate patient feedback data representing the level of severity of the at least one negative side effect of blood treatment selected by the patient the at least one negative side effect of blood treatment comprising at least one of nausea, tiredness, dizziness, body temperature irregularity, cramping, itching, or headaches, and
  a signal transceiver configured to send the patient feedback data to the controller of the blood treatment machine.

20. The system according to claim 19, wherein the patient comfort feedback mechanism is wirelessly connected to the blood treatment machine.

21. The system according to claim 19, wherein the treatment parameter is the ultrafiltration rate.

22. The system according to claim 21, wherein the controller reduces the ultrafiltration rate in response to the level of severity of the at least one negative side effect of blood treatment selected by the patient.

23. The system according to claim 19, wherein the controller displays the patient feedback data on a user interface of the blood treatment machine.

24. The system according to claim 19, wherein the patient comfort feedback mechanism provides at least three levels of severity of the at least one negative side effect of blood treatment.

25. The system according to claim 19, wherein the controller is configured to adjust the treatment parameter to a predetermined level corresponding to the level of severity of the at least one negative side effect of blood treatment selected by the patient.

26. A method for blood treatment comprising:
performing blood treatment,
receiving patient input comprising a level of severity of at least one negative side effect of blood treatment selected by a patient via a patient comfort feedback mechanism configured to be adjusted by the patient to select the level of severity of the at least one negative side effect of blood treatment currently being experienced by the patient, the at least one negative side effect of blood treatment comprising at least one of nausea, tiredness, dizziness, body temperature irregularity, cramping, itching, or headaches, and
adjusting a parameter of the blood treatment based on the level of severity of the at least one negative side effect of blood treatment selected by the patient, wherein the parameter is at least one of: a sodium level, an ultrafiltration rate, a saline infusion rate, a dialysate flow rate, a treatment time, a blood flow rate, a frequency of blood pressure measurements, a calcium level, a pump rate, a drain percentage, a dialysate dwell time, and fluid temperatures.

27. The method according to claim 26, wherein the adjusting the parameter of the blood treatment comprises adjusting the ultrafiltration rate.

28. The method according to claim 26, wherein adjusting the parameter of the blood treatment based on the level of severity of the at least one negative side effect of blood treatment selected by the patient comprises adjusting the parameter of the blood treatment to a predetermined level corresponding to the level of severity of the at least one negative side effect of blood treatment selected by the patient.

29. The method according to claim 26, wherein the patient comfort feedback mechanism provides at least three levels of severity of the at least one negative side effect of blood treatment.

* * * * *